(12) United States Patent
Qi

(10) Patent No.: US 11,919,905 B2
(45) Date of Patent: Mar. 5, 2024

(54) SUBSTITUTED BENZO[F]IMIDAZO[1,2-A][1,4]DIAZEPINES AS ANESTHETICS

(71) Applicant: HANGZHOU ADAMERCK PHARMLABS INC., Zhejiang (CN)

(72) Inventor: Youmao Qi, Zhejiang (CN)

(73) Assignee: Hangzhou Adamerck Pharmlabs, Inc., Zhejiang (CN)

( * ) Notice: Subject to any disclaimer, the term of this patent is extended or adjusted under 35 U.S.C. 154(b) by 849 days.

(21) Appl. No.: 16/958,977

(22) PCT Filed: Dec. 28, 2018

(86) PCT No.: PCT/CN2018/124969
§ 371 (c)(1),
(2) Date: Jul. 24, 2020

(87) PCT Pub. No.: WO2019/129216
PCT Pub. Date: Jul. 4, 2019

(65) Prior Publication Data
US 2022/0372037 A1 Nov. 24, 2022

(30) Foreign Application Priority Data
Dec. 28, 2017 (CN) .......................... 20171145455.9

(51) Int. Cl.
| | |
|---|---|
| A61K 31/5517 | (2006.01) |
| A61P 23/00 | (2006.01) |
| C07D 487/04 | (2006.01) |
| C07D 487/12 | (2006.01) |

(52) U.S. Cl.
CPC ............ C07D 487/04 (2013.01); A61P 23/00 (2018.01)

(58) Field of Classification Search
CPC .................. A61K 31/5517; C07D 487/12
USPC .......................................... 514/220; 540/586
See application file for complete search history.

(56) References Cited

FOREIGN PATENT DOCUMENTS

| | | |
|---|---|---|
| CA | 999860 | 11/1976 |
| CN | 104768557 | 8/2015 |
| CN | 108033964 | 5/2018 |
| FR | 2183716 | 12/1973 |
| WO | 0069836 | 11/2000 |

OTHER PUBLICATIONS

International Search Report for PCT/CN2018/124969, issued Mar. 29, 2019.

*Primary Examiner* — Douglas M Willis
(74) *Attorney, Agent, or Firm* — Ice Miller LLP

(57) ABSTRACT

Disclosed are a pyridyl imidazobenzodiazepine propionate (compound 1) and the synthesis and use thereof. Also provided are intermediates for the preparation. Compound 1 provided by the present invention has an obvious venous anesthesia activity equivalent to that of the positive control drug remimazolam p-toluenesulfonate or remimazolam besylate. In addition, compound 1 can be significantly reduced in mouse model experiments, and same can even overcome common limb jitters, head tilting, opisthotonus and other side effects caused by the remimazolam besylate or remimazolam p-toluenesulfonate as a drug during development in preclinical animal experiments, thereby allowing same to be used in the preparation of intravenous anesthetics. The structural general formula of compound 1 is as follows, wherein each group and substituent are as defined in the description.

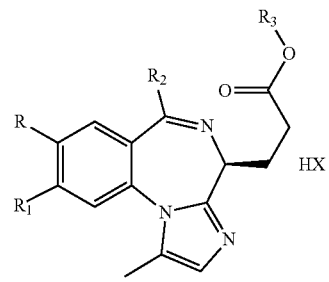

12 Claims, 3 Drawing Sheets

SUBSTITUTED BENZO[F]IMIDAZO[1,2-A][1,4]DIAZEPINES AS ANESTHETICS

CROSS-REFERENCE TO RELATED APPLICATION

This application is a Section 371 of International Application No. PCT/CN2018/124969, filed Dec. 28, 2018, which was published in the Chinese language on Jul. 4, 2019, under International Publication No. WO 2019/129216 A1, which claims priority under 35 U.S.C. § 119(b) to CN Application No. 201711454554.9, filed Dec. 28, 2017, the disclosures of which are incorporated herein by reference in their entirety.

TECHNICAL FIELD

The present invention belongs to the field of medicine and chemical industry, and relates to a new pyridyl imidazobenzodiazepine propionate compound and its synthesis and application in the preparation of intravenous anesthetic drugs.

BACKGROUND ART

Remimazolam is a new type of ultra-short-acting systemic sedative anesthetic, and it is a soluble BZ derivatives, and it has a great affinity on BZ receptors in the cerebral cortex, limbic system, midbrain and brainstem spinal cord, and it can quickly and temporarily act on the 4 subtypes of γ-aminobutyric acid A (GABAA) receptor. But remimazolam has a higher affinity on the α1 subtype of the receptor, which can promote the binding of GABA and the receptor, with increased Cl⁻ channel opening frequency and more Cl⁻ influx, resulting in hyperpolarization of nerve cells, thus resulting in a nerve suppression effect. Then, it is found that Remimazolam besylate or Remimazolam p-toluenesulfonate as a drug under study commonly have side effects such as limb jitters, head tilting, opisthotonus in the pre-clinical animal experiments, so it is expected to develop a safer, new ultra-short-acting sedative anesthetic drugs for intravenous administration in the following clinical treatment protocols: operation of sedation, general anesthesia and ICU sedation.

SUMMARY OF THE INVENTION

The present invention provides a new pyridyl imidazobenzodiazepine propionate compound 1, which has the following structural general formula:

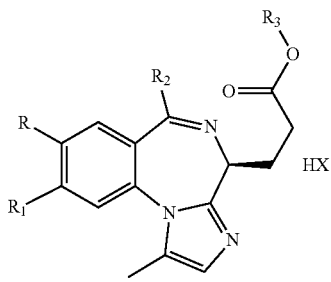

1 wherein, R represents various alkyl having a short carbon chain, trifluoromethyl, methoxy, nitro, fluorine, chlorine, or bromine, etc.;

$R_1$ represents various alkyl having a short carbon chain, trifluoromethyl, methoxy, nitro, fluorine, chlorine, or bromine, etc.;

$R_2$ represents a pyridine ring with nitrogen at position 2, 3 or 4;

$R_3$ represents various alkyl having a short carbon chain;

HX represents any acceptable pharmaceutical inorganic acids and organic acids, preferably p-toluenesulfonic acid.

In another preferred embodiment, R is selected from the group consisting of halogen, nitro, halogenated C1-C6 alkyl, C1-C6 alkyl and C1-C6 alkoxy.

In another preferred embodiment, $R_1$ is selected from the group consisting of halogen, nitro, halogenated C1-C6 alkyl, C1-C6 alkyl and C1-C6 alkoxy.

In another preferred embodiment, the various alkyl having a short carbon chain is C1-C6 alkyl, such as methyl, ethyl, propyl, isopropyl, butyl, isobutyl, tert-butyl, n-pentyl, isopentyl, neopentyl, n-hexyl, or a similar group.

In another preferred embodiment, the halogenated C1-C6 alkyl is a C1-C6 alkyl substituted with one or more (such as 2 or 3) halogen.

In another preferred embodiment, halogen is selected from the group consisting of F, Cl, Br and I.

In another preferred embodiment, the halogenated C1-C6 alkyl is a fluorinated C1-C6 alkyl.

In another preferred embodiment, the halogenated C1-C6 alkyl is preferably trifluoromethyl.

In another preferred embodiment, the C1-C6 alkoxy is a linear or branched alkoxy including 1-6 carbon atoms, such as methoxy, ethoxy, propoxy, isopropoxy, butoxy, isobutoxy, tert-butoxy, or a similar group.

In another preferred embodiment, $R_2$ is a pyridine ring with nitrogen at position 2, 3 or 4.

In another preferred embodiment, $R_3$ is C1-C6 alkyl.

In another preferred embodiment, HX is a pharmaceutically acceptable acid selected from the group consisting of inorganic acids, organic acids and amino acids.

In another preferred embodiment, the inorganic acids include (but are not limited to): hydrochloric acid, hydrobromic acid, hydrofluoric acid, sulfuric acid, nitric acid, or phosphoric acid.

In another preferred embodiment, the organic acids include (but are not limited to): formic acid, acetic acid, trifluoroacetic acid, propionic acid, oxalic acid, malonic acid, succinic acid, fumaric acid, maleic acid, lactic acid, malic acid, tartaric acid, citric acid, picric acid, benzoic acid, methanesulfonic acid, ethanesulfonic acid, p-toluenesulfonic acid, benzenesulfonic acid, or naphthalenesulfonic acid.

In another preferred embodiment, the organic acid is selected from the group consisting of p-toluenesulfonic acid and benzenesulfonic acid, preferably is p-toluenesulfonic acid.

In another preferred embodiment, the amino acids include (but are not limited to): citrulline, ornithine, arginine, lysine, proline, phenylalanine, aspartic acid, or glutamic acid.

In another preferred embodiment, the amino acid has a configuration selected from the group consisting of racemic configuration, D configuration, and L configuration.

In another preferred embodiment, R is selected from the group consisting of halogen, nitro, C1-C6 alkyl, halogenated C1-C6 alkyl, C3-C8 cycloalkyl, halogenated C3-C8 cycloalkyl, C1-C6 alkoxy, and halogenated C1-C6 alkoxy;

R₁ is selected from the group consisting of halogen, nitro, C1-C6 alkyl, halogenated C1-C6 alkyl, C3-C8 cycloalkyl, halogenated C3-C8 cycloalkyl, C1-C6 alkoxy, and halogenated C1-C6 alkoxy;
R₂ is a pyridine ring with nitrogen at position 2, 3 or 4;
R₃ is C1-C6 alkyl;
HX is a pharmaceutically acceptable acid selected from the group consisting of inorganic acids, organic acids, and amino acids.

In another preferred embodiment, R and R₁ are different.

In another preferred embodiment, R is F; R₁ is C1-C6 alkyl; R₂ is a pyridine ring with nitrogen at position 2;
R₃ is C1-C6 alkyl;
HX is a pharmaceutically acceptable acid selected from the group consisting of inorganic acids, organic acids, and amino acids.

In another preferred embodiment, R is C1-C6 alkyl; R₁ is F; R₂ is a pyridine ring with nitrogen at position 3;
R₃ is C1-C6 alkyl;
HX is a pharmaceutically acceptable acid selected from the group consisting of inorganic acids, organic acids, and amino acids.

In another preferred embodiment, the compound 1 is selected from the group consisting of:

| Number | Compound |
|---|---|
| 1-1 | 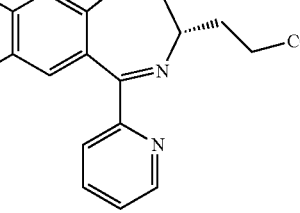 |
| 1-2 | 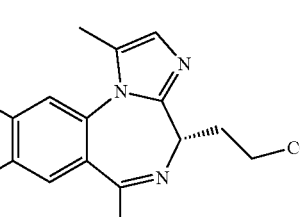 |
| 1-3 | 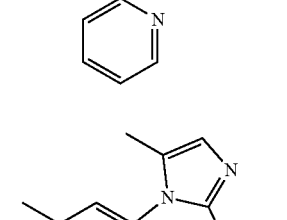 |
| 1-4 | 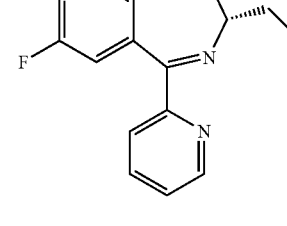 |

-continued
| Number | Compound | | |
|---|---|---|---|
| 1-5 | 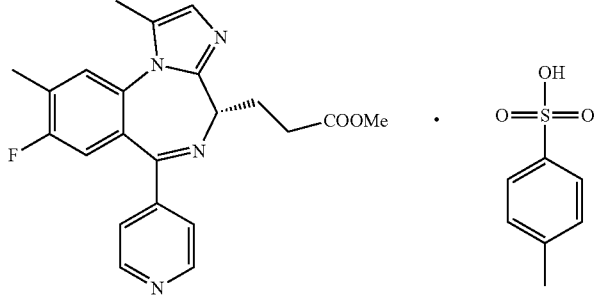 [SMILES: COC(=O)CC[C@@H]1N=C(c2ccncc2)c2cc(F)c(C)cc2-n2c(C)cnc21 ; Cc1ccc(S(=O)(=O)O)cc1] | · | 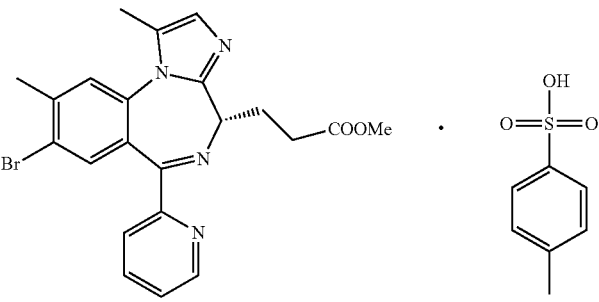 [SMILES: COC(=O)CC[C@@H]1N=C(c2ccccn2)c2cc(Br)c(C)cc2-n2c(C)cnc21 ; Cc1ccc(S(=O)(=O)O)cc1] |
| 1-6 | 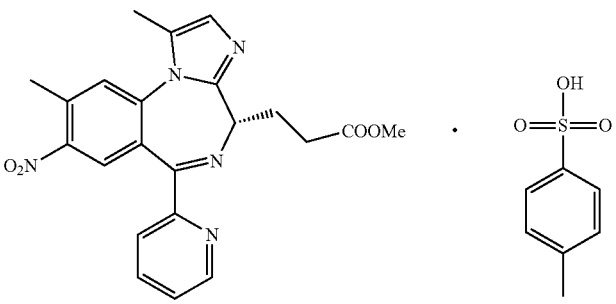 [SMILES: COC(=O)CC[C@@H]1N=C(c2ccccn2)c2cc([N+](=O)[O-])c(C)cc2-n2c(C)cnc21 ; Cc1ccc(S(=O)(=O)O)cc1] | · | |
| 1-7 | 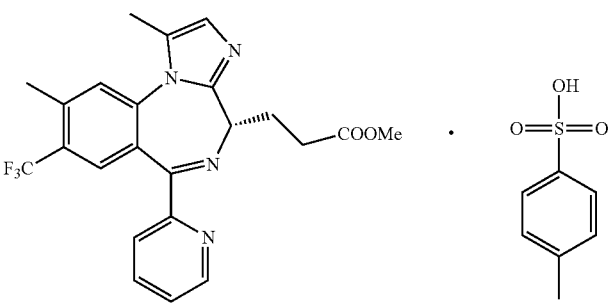 [SMILES: COC(=O)CC[C@@H]1N=C(c2ccccn2)c2cc(C(F)(F)F)c(C)cc2-n2c(C)cnc21 ; Cc1ccc(S(=O)(=O)O)cc1] | · | |
| 1-8 | 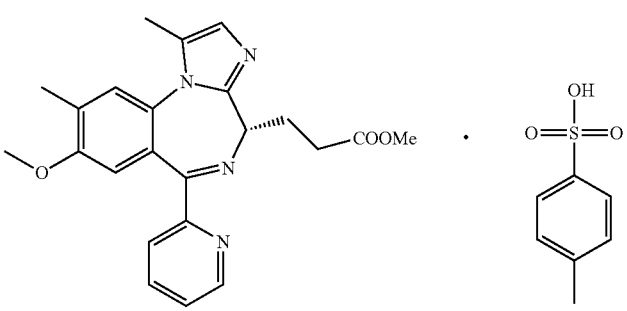 [SMILES: COC(=O)CC[C@@H]1N=C(c2ccccn2)c2cc(OC)c(C)cc2-n2c(C)cnc21 ; Cc1ccc(S(=O)(=O)O)cc1] | · | |
| 1-9 | 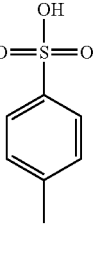 | · | |

-continued
| Number | Compound |
|---|---|
| 1-10 | 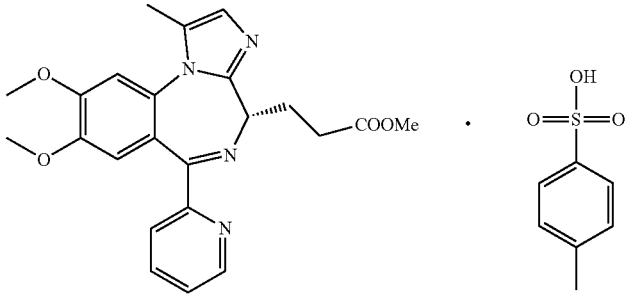 [SMILES: COC(=O)CC[C@@H]1N=C(c2ccccn2)c2cc(OC)c(OC)cc2-n2c(C)cnc21 ; Cc1ccc(S(=O)(=O)O)cc1] |
| 1-11 | 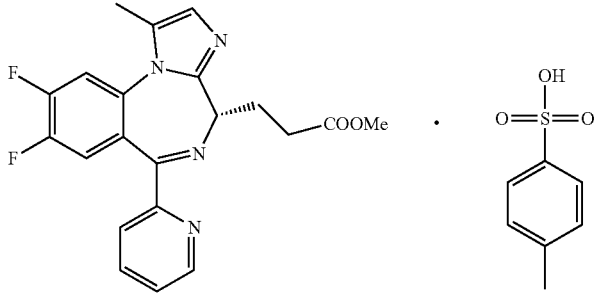 [SMILES: COC(=O)CC[C@@H]1N=C(c2ccccn2)c2cc(F)c(F)cc2-n2c(C)cnc21 ; Cc1ccc(S(=O)(=O)O)cc1] |
| 1-12 | 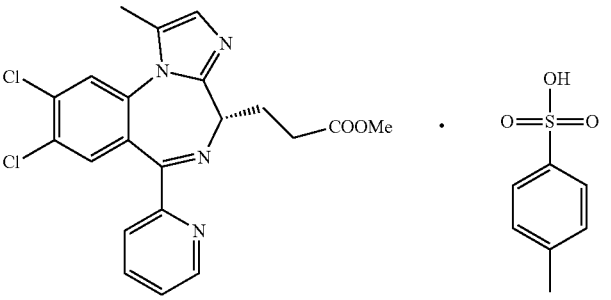 [SMILES: COC(=O)CC[C@@H]1N=C(c2ccccn2)c2cc(Cl)c(Cl)cc2-n2c(C)cnc21 ; Cc1ccc(S(=O)(=O)O)cc1] |
| 1-13 | 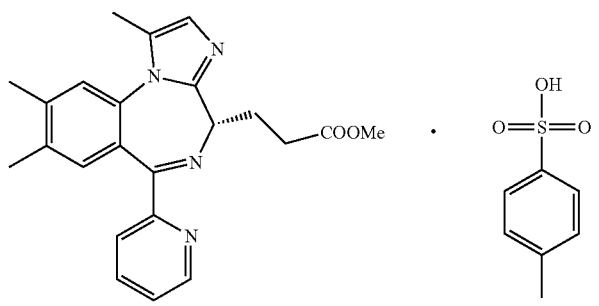 [SMILES: COC(=O)CC[C@@H]1N=C(c2ccccn2)c2cc(C)c(C)cc2-n2c(C)cnc21 ; Cc1ccc(S(=O)(=O)O)cc1] |
| 1-14 | 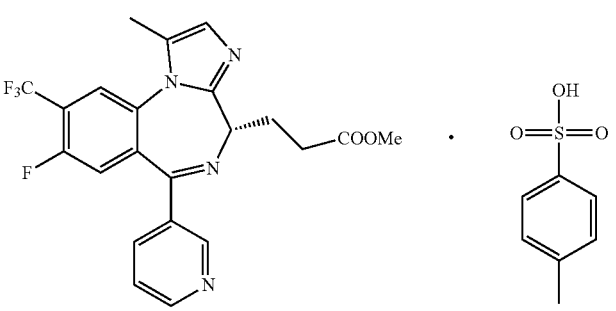 [SMILES: COC(=O)CC[C@@H]1N=C(c2cccnc2)c2cc(F)c(C(F)(F)F)cc2-n2c(C)cnc21 ; Cc1ccc(S(=O)(=O)O)cc1] |

-continued

| Number | Compound |
|---|---|
| 1-15 | ![compound 1-15 structure with tosylate] |
| 1-16 | ![compound 1-16 structure with tosylate] |
| 1-17 | ![compound 1-17 structure with tosylate] |

The present invention also provides a 2-(Boc-L-glutamate-5 ester acyl)amino-3,4-disubstituted benzoylpyridine 4, which can be used as an intermediate for synthesis 1 and has the following structure general formula:

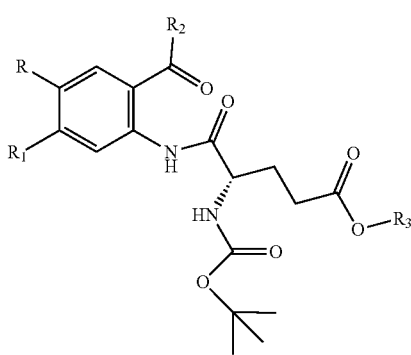

wherein R, $R_1$, $R_2$, and $R_3$ are as described above.

The present invention also provides a 2-(L-glutamate-5 ester acyl)amino-3,4-disubstituted benzoylpyridine salt 6, which has the following structure general formula:

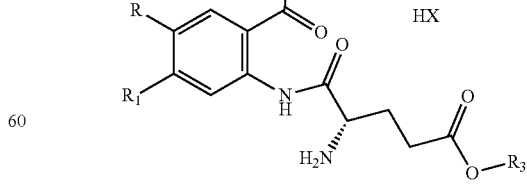

wherein R, $R_1$, $R_2$, $R_3$, and HX are as described above.

The present invention also provides a 3,4-disubstituted benzodiazepine propionate 7 having the following structure general formula:

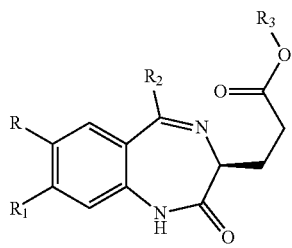

7 wherein R, $R_1$, $R_2$, and $R_3$ are as described above.

The present invention also provides an I—N-(3,4-disubstituted benzodiazepine propionate group)amino-2-propanol 9, which has the following structure general formula:

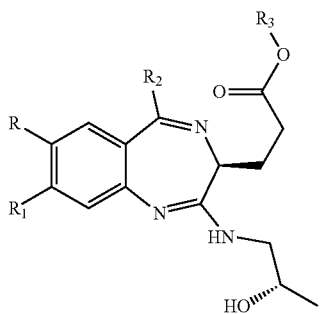

9 wherein R, $R_1$, $R_2$, and $R_3$ are as described above.

The present invention also provides a pyridyl imidazobenzodiazepine propionate compound 10, which has the following structure general formula:

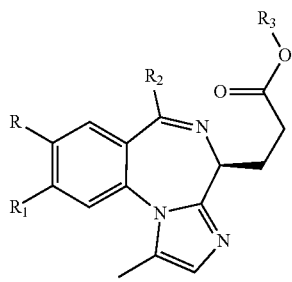

10 wherein, R is selected from the group consisting of various alkyls having a short carbon chain, trifluoromethyl, methoxy, nitro, fluorine, chlorine, and bromine;
$R_1$ is selected from the group consisting of various alkyls having a short carbon chain, trifluoromethyl, methoxy, nitro, fluorine, chlorine, and bromine;
$R_2$ is a pyridine ring with nitrogen at position 2, 3 or 4;
$R_3$ is various alkyl having a short carbon chain.

In another preferred embodiment, R is selected from the group consisting of halogen, nitro, C1-C6 alkyl, halogenated C1-C6 alkyl, C3-C8 cycloalkyl, halogenated C3-C8 cycloalkyl, C1-C6 alkoxy, and halogenated C1-C6 alkoxy.

In another preferred embodiment, $R_1$ is selected from the group consisting of halogen, nitro, C1-C6 alkyl, halogenated C1-C6 alkyl, C3-C8 cycloalkyl, halogenated C3-C8 cycloalkyl, C1-C6 alkoxy, and halogenated C1-C6 alkoxy.

In another preferred embodiment, the various alkyl having a short carbon chain is C1-C6 alkyl, such as methyl, ethyl, propyl, isopropyl, butyl, isobutyl, tert-butyl, n-pentyl, isopentyl, neopentyl, n-hexyl, or a similar group.

In another preferred embodiment, the halogenated C1-C6 alkyl is a C1-C6 alkyl substituted with one or more (such as 2 or 3) halogen.

In another preferred embodiment, halogen is selected from the group consisting of F, Cl, Br and I.

In another preferred embodiment, the halogenated C1-C6 alkyl is a fluorinated C1-C6 alkyl.

In another preferred embodiment, the halogenated C1-C6 alkyl is preferably trifluoromethyl.

In another preferred embodiment, the C1-C6 alkoxy is a linear or branched alkoxy including 1-6 carbon atoms, such as methoxy, ethoxy, propoxy, isopropoxy, butoxy, isobutoxy, tert-butoxy, or a similar group.

In another preferred embodiment, $R_2$ is a pyridine ring with nitrogen at position 2, 3 or 4.

In another preferred embodiment, $R_3$ is C1-C6 alkyl.

In another preferred embodiment, R is selected from the group consisting of halogen, nitro, C1-C6 alkyl, halogenated C1-C6 alkyl, C3-C8 cycloalkyl, halogenated C3-C8 cycloalkyl, C1-C6 alkoxy, and halogenated C1-C6 alkoxy;

$R_1$ is selected from the group consisting of halogen, nitro, C1-C6 alkyl, halogenated C1-C6 alkyl, C3-C8 cycloalkyl, halogenated C3-C8 cycloalkyl, C1-C6 alkoxy, and halogenated C1-C6 alkoxy;

$R_2$ is a pyridine ring with nitrogen at position 2, 3 or 4;

$R_3$ is C1-C6 alkyl.

In another preferred embodiment, R and $R_1$ are different.

In another preferred embodiment, R is F; $R_1$ is C1-C6 alkyl; $R_2$ is a pyridine ring with nitrogen at position 2;

$R_3$ is C1-C6 alkyl.

In another preferred embodiment, R is C1-C6 alkyl; $R_1$ is F; $R_2$ is a pyridine ring with nitrogen at position 3;

$R_3$ is C1-C6 alkyl.

In another preferred embodiment, the compound 10 is selected from the group consisting of:

| Compound |
| --- |
| 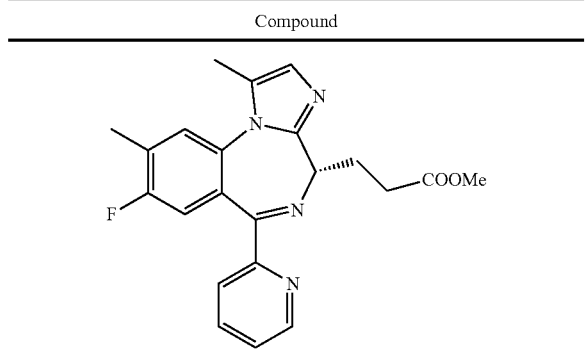 |

| Compound |
|---|
| 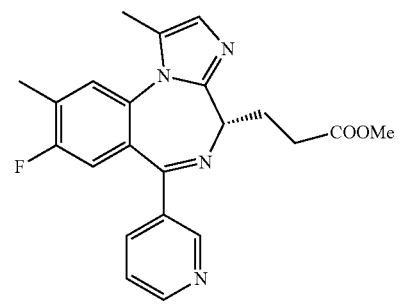 [SMILES: COC(=O)CC[C@@H]1N=C(c2cccnc2)c2cc(F)c(C)cc2-n2c(C)cnc21] |
| 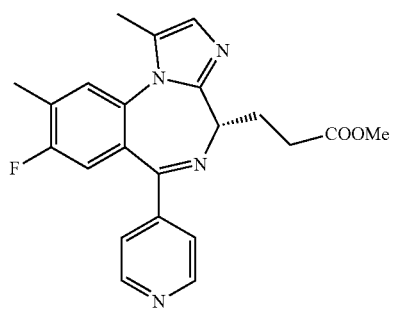 [SMILES: COC(=O)CC[C@@H]1N=C(c2ccncc2)c2cc(F)c(C)cc2-n2c(C)cnc21] |
| 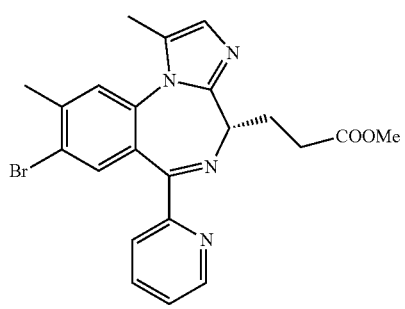 |
| 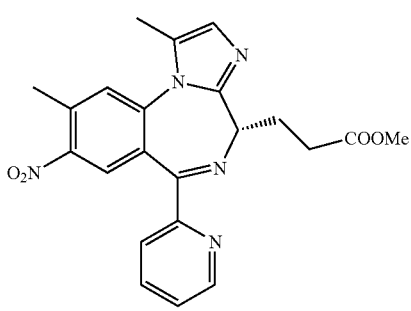 [SMILES: COC(=O)CC[C@@H]1N=C(c2ccccn2)c2cc([N+](=O)[O-])c(C)cc2-n2c(C)cnc21] |
| 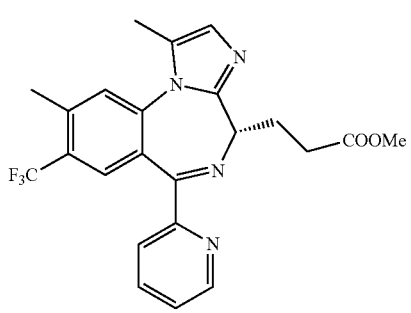 [SMILES: COC(=O)CC[C@@H]1N=C(c2ccccn2)c2cc(C(F)(F)F)c(C)cc2-n2c(C)cnc21] |
| Compound |
|---|
| 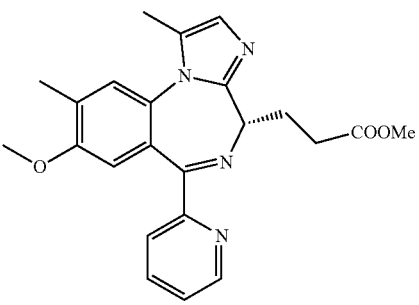 [SMILES: COC(=O)CC[C@@H]1N=C(c2ccccn2)c2cc(OC)c(C)cc2-n2c(C)cnc21] |
| 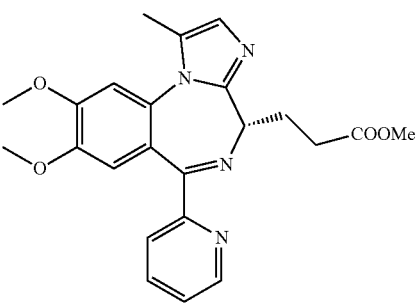 [SMILES: COC(=O)CC[C@@H]1N=C(c2ccccn2)c2cc(OC)c(OC)cc2-n2c(C)cnc21] |
| 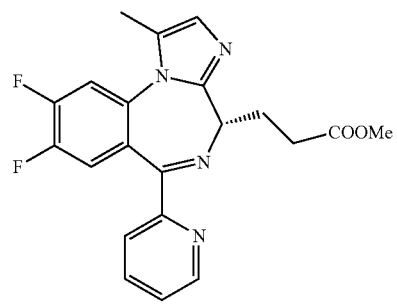 [SMILES: COC(=O)CC[C@@H]1N=C(c2ccccn2)c2cc(F)c(F)cc2-n2c(C)cnc21] |
| 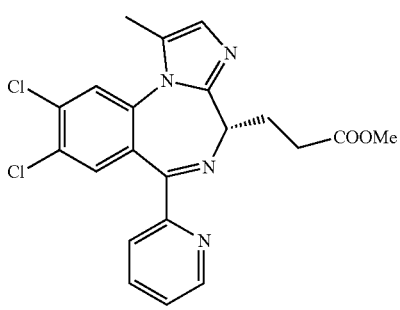 [SMILES: COC(=O)CC[C@@H]1N=C(c2ccccn2)c2cc(Cl)c(Cl)cc2-n2c(C)cnc21] |
| 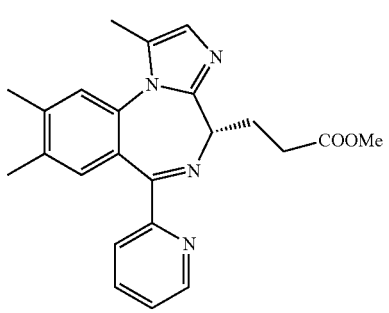 [SMILES: COC(=O)CC[C@@H]1N=C(c2ccccn2)c2cc(C)c(C)cc2-n2c(C)cnc21] |

| Compound |
|---|
| 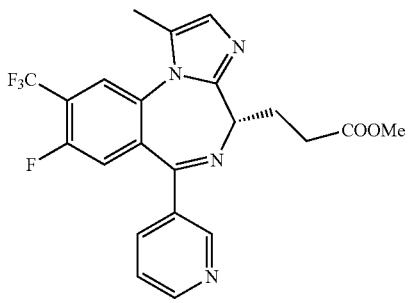 [SMILES: COC(=O)CC[C@@H]1N=C(c2cccnc2)c2cc(F)c(C(F)(F)F)cc2-n2c(C)cnc21] |
| 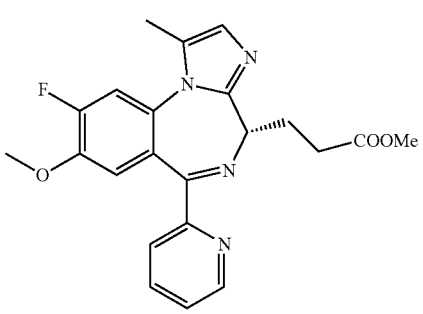 [SMILES: COC(=O)CC[C@@H]1N=C(c2ccccn2)c2cc(OC)c(F)cc2-n2c(C)cnc21] |
| 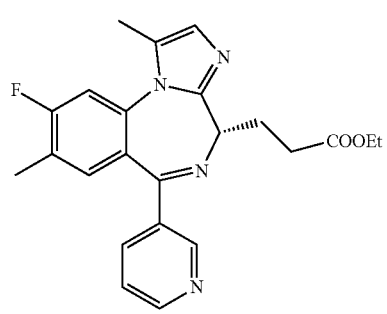 [SMILES: CCOC(=O)CC[C@@H]1N=C(c2cccnc2)c2cc(C)c(F)cc2-n2c(C)cnc21] |

| Compound |
|---|
| 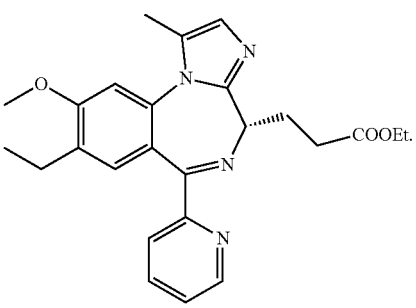 [SMILES: CCOC(=O)CC[C@@H]1N=C(c2ccccn2)c2cc(CC)c(OC)cc2-n2c(C)cnc21] |

The present invention also provides a method for preparing the pyridyl imidazobenzodiazepine propionate compound 1, which is realized by the following steps:

anthranilopyridine 2 with various substituents at the 3 and 4 positions and Boc-L-glutamate-5 ester 3 are used as the starting materials to generate 2-(Boc-L-glutamate-5 esteracyl)amino-3,4-disubstituted benzoylpyridine 4 in the presence of DCC; the Boc protecting group is removed under the action of acid 5 to obtain 2-(L-glutamic acid-5esteracyl)amino-3,4-disubstituted benzoylpyridine salt 6; intramolecular condensation occurs in the presence of sodium bicarbonate to obtain 3,4-disubstituted benzodiazepine propionate 7, which then reacts wiI(R)-1-amino-2-propanol 8 to produce (S)—N-(3,4-disubstituted benzodiazepine propionate) amino-2-propanol 9; oxidative ring-closure reaction with DMP yields pyridyl imidazobenzo diazepine propionate 10; the target product pyridyl imidazobenzodiazepine propionate salt compound 1 is obtained through salt formation reaction with acid 5.

The reaction formula is as follows:

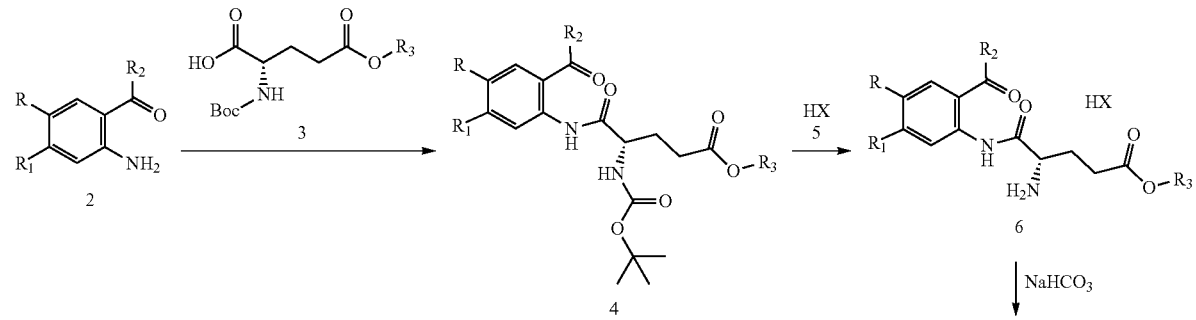

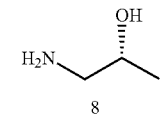
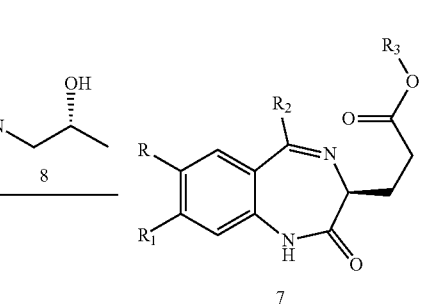
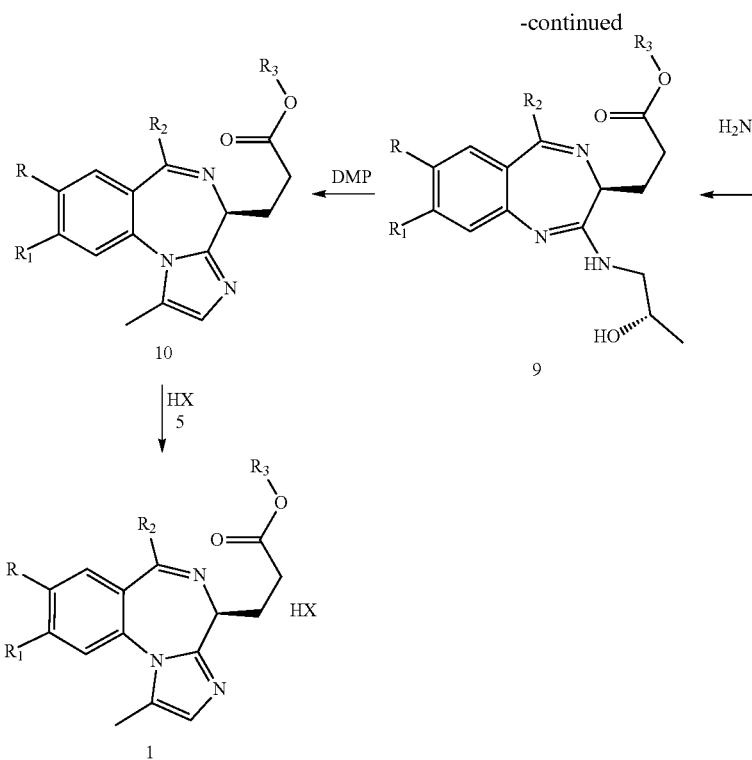

wherein, R, $R_1$, $R_2$, $R_3$, and HX are as described above; DMP stands for Dess-Martin Periodinane.

The equivalent ratio of the reaction of compound 2, compound 3 and DCC is 1:0.9~1.1:1~1.5.

The equivalent ratio of the reaction of compound 6 and sodium bicarbonate is 1:10~20.

The equivalent ratio of the reaction of compounds 7 and 8 is 1:2~3.

The equivalent ratio of the reaction of compound 9 and DMP is 1:3~6, and the reaction temperature is between 30-60° C.

The equivalent ratio of the reaction of compound 10 and acid 5 in the step is 1:1-2, preferably 1:1.

HX is preferably p-toluenesulfonic acid.

The present invention also provides a pharmaceutical composition, wherein the pharmaceutical composition comprises:

1) an anesthetically effective amount of one or more of the above compound 1 and/or compound 10; and
2) a pharmaceutically acceptable carrier.

The present invention also provides a use of the pyridyl imidazobenzodiazepine propionate compound 1 for preparing intravenous anesthetic drugs.

The present invention also provides an anesthesia method, which comprises administering an anesthesia effective amount of the above compound 1 and/or compound 10 to a subject to be anesthetized.

In another preferred embodiment, the anesthesia method is used in a treatment plan selected from the group consisting of: operation of sedation, general anesthesia and ICU sedation.

The target products 1, 4, 6, 7, 9 and 10 synthesized according to the above reactions are all new compounds, and their structures were characterized by 1H NMR and ESI-MS. Through animal model test research, the results show that: compound 1 has obvious intravenous anesthesia activity, and the intravenous anesthesia activity of compound 1 is equivalent to that of the positive control drug remimazolam p-toluenesulfonate or remimazolam besylate.

In addition, the inventor surprisingly finds that, in mouse model experiments, compound 1 can significantly reduce and can even overcome common limb jitters, head till pisthotonoshotonus and other side effects caused by the remimazolam besylate or remimazolam p-toluenesulfonate as a drug during development in preclinical animal experiments, so it may have the significance of further development into clinical medicine.

It should be understooI that in the Iresent invention, any of the technical features specifically described above and below (such as in the Examples) can be combined with each other, which will not redundantly be described one by one herein.

DETAILED DESCRIPTION OF THE INVENTION

Figure 1:
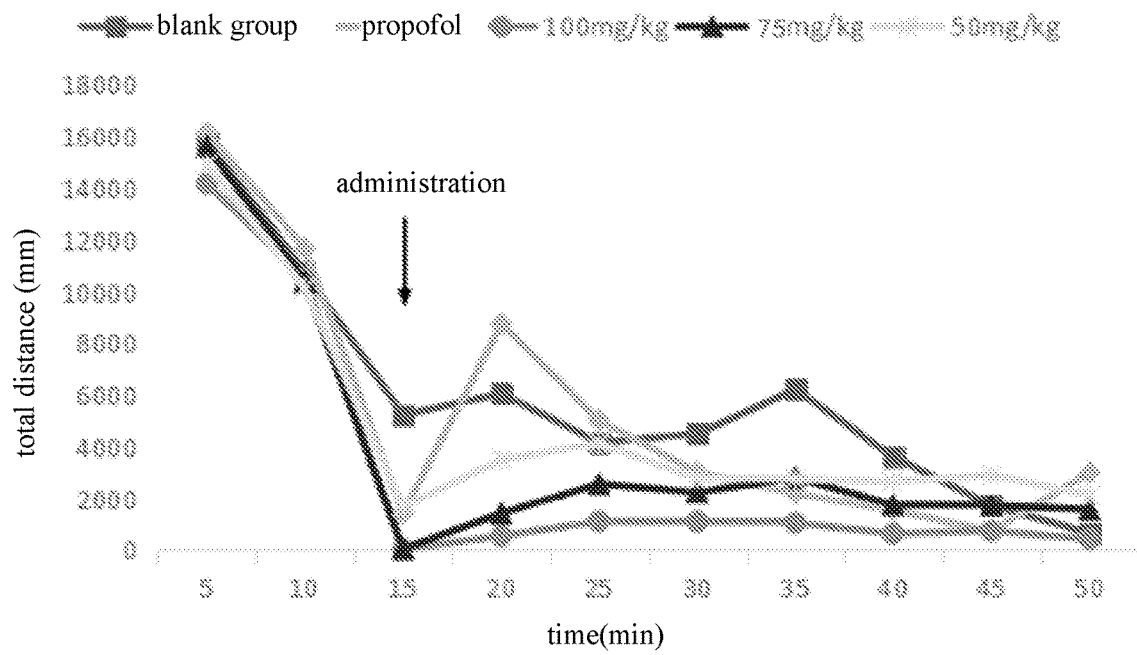
FIG. 1 shows the effect of a single administration of compound 1-2 in Example 27 on the total distance of mice's autonomous activities.

After long time and intensive research, the inventor unexpectedly prepared a compound for anesthesia with high safety, rapid onset and/or rapid recovery by adjusting the structure of the compound. Specifically, compared to the existing remimazolam (or its p-toluenesulfonate or besylate) mono-substituted at positions R or $R_1$, the inventor finds that double substitution at R and $R_1$ can obtain compounds for anesthesia with higher safety and better overall performance. Further, compared to compounds with Br as one of the substituents double substituted at R and $R_1$, compounds with F as one of the substituents have better bio-penetration and better target organ selectivity and are basically non-toxic. Furthermore, when R is F, $R_1$ is C1-C6 alkyl, and $R_2$ is a pyridyl with N at position 2 (such as compound 1-2), the compound has extremely excellent comprehensive anesthetic properties. On this basis, the inventors have completed the present invention.

TERMS

In the present invention, unless specifically indicated, the terms used have the general meanings well known to those skilled in the art.

In the present invention, the term "halogen" refers to F, Cl, Br or I.

In the present invention, "C1-C6 alkyl" refers to a linear or branched alkyl including 1-6 carbon atoms, such as methyl, ethyl, propyl, isopropyl, butyl, isobutyl, tert-butyl, neopentyl, tert-pentyl, or a similar group.

In the present invention, the term "C3-C8 cycloalkyl" refers to a cyclic alkyl having 3 to 8 carbon atoms in the ring, and includes, but not limited to, cyclopropyl, cyclobutyl, cyclopentyl, cyclohexyl, cycloheptyl, cyclooctyl, etc.

In the present invention, the term "halogenated" means substituted by halogen.

In the present invention, the term "C1-C6 alkoxy" refers to a linear or branched alkoxy having 1 to 6 carbon atoms, and includes, but not limited to, methoxy, ethoxy, propoxy, isopropoxy, butoxy, etc. It is preferably C1-C4 alkoxy.

In the present invention, the term "substituted" means that one or more hydrogen atoms on a specific group are replaced with a specific substituent. The specific substituents are the substituents described correspondingly in the foregoing, or the substituents appearing in the respective embodiments. Unless otherwise specified, a substituted group may have a substituent selected from a specific group at any substitutable position of the group, and the substituents may be the same or different at each position. Those skilled in the art will understand that the combinations of substituents contemplated by the present invention are those that are stable or chemically achievable. The substituents are, for example (but not limited to): halogen, hydroxyl, carboxyl (—COOH), C1-C6 alkyl, C2-C6 alkenyl, C2-C6 alkynyl, C3-C8 cycloalkyl, 3-12 membered heterocyclic group, aryl, heteroaryl, C1-C8 aldehyde group, C2-C10 acyl, C2-C10 ester group, amino, C1-C6 alkoxy, C1-C10 sulfonyl group and the like.

Compound 1

The present invention provides a new pyridyl imidazobenzodiazepine propionate compound 1, which has the following structural general formula:

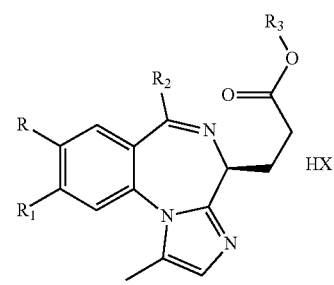

1

Wherein, R, $R_1$, $R_2$, $R_3$ and HX are as defined above.

In another preferred embodiment, any one of R, $R_1$, $R_2$, $R_3$ and HX in compound 1 is a corresponding group in the specific compound of the present invention.

Compound 10

The present invention also provides a pyridyl imidazobenzodiazepine propionate compound 10, which has the following structure general formula:

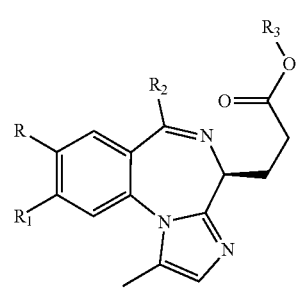

10 wherein, R, $R_1$, $R_2$, and $R_3$ are as defined above.

Peparation method The preparation methods of compound 1 or compound 10 of the present invention are described in more detail below, but these specific methods do not constitute any limitation to the present invention. The compounds of the present invention may also be conveniently prepared by optionally combining various synthetic methods described in the specification or known in the art, and such combinations are readily made by those skilled in the art to which the present invention pertains.

Typically, the preparation process of the compounds of the present invention is as follows, wherein the starting materials and reagents used are commercially available unless otherwise specified.

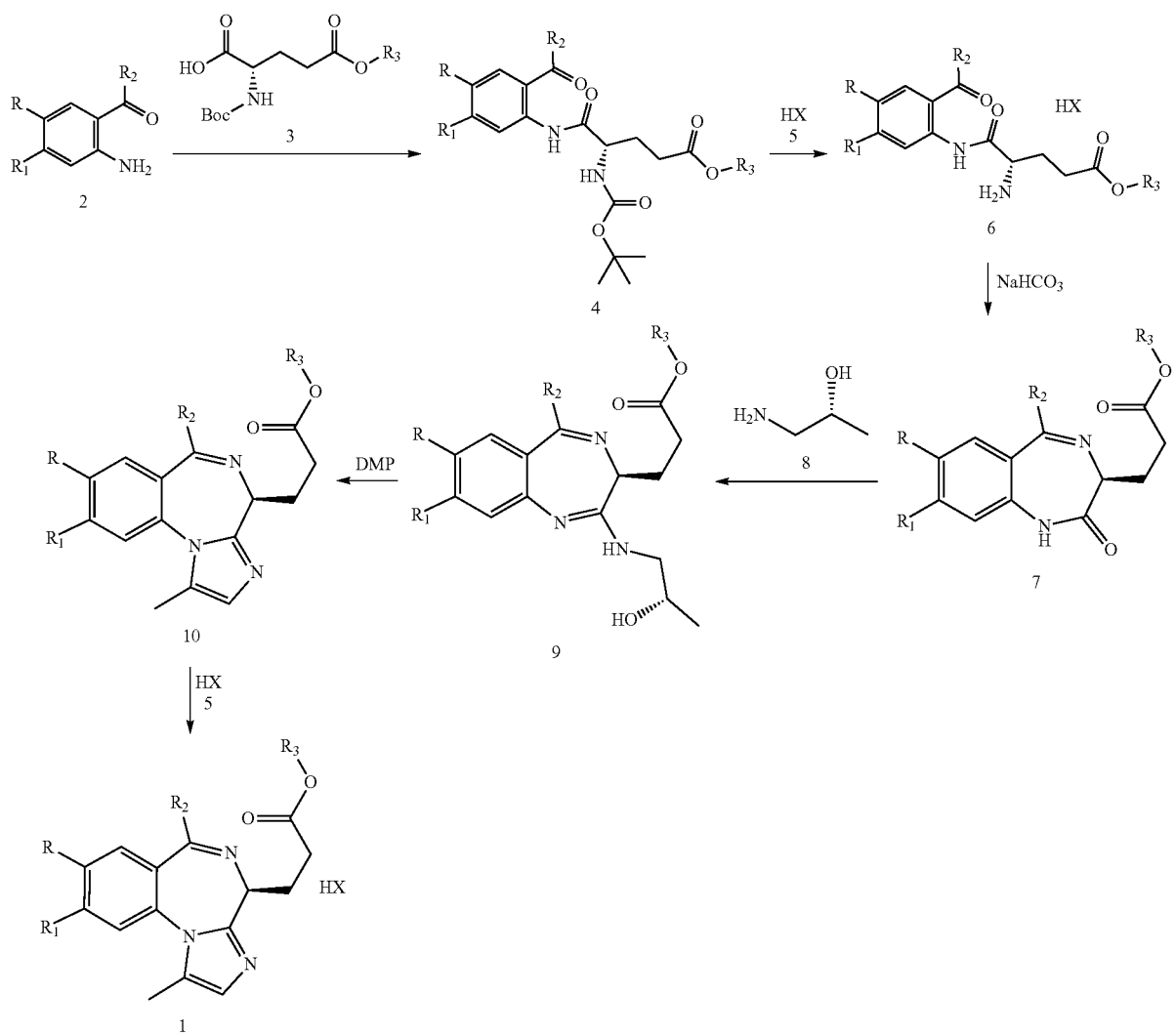

wherein R, $R_1$, $R_2$, $R_3$ and HX are as defined above.

Pharmaceutical Composition and Method for Administration

The present invention also provides a pharmaceutical composition, wherein the pharmaceutical composition comprises:
1) an anesthetically effective amount of one or more of the above compound 1 and/or compound 10; and
2) a pharmaceutically acceptable carrier.

In another preferred embodiment, the "anesthetically effective amount" means that the amount of the compound is sufficient to achieve the anesthetic effect without causing serious side effects.

In another preferred embodiment, the "anesthetically effective amount" is 0.1-500 mg, preferably 0.5-300 mg, more preferably 1-200 mg, relative to a person weighing 60 kg.

In another preferred embodiment, the "pharmaceutically acceptable carrier" refers to a substance including (but not limited to) the following group: water for injection, vegetable oil (such as sesame oil, soybean oil, etc.), sodium chloride, glycerin, glucose, ethanol, polyethylene glycol and propylene glycol. Appropriate amounts of excipients, buffers, wetting agents or emulsifiers can also be added as needed.

In another preferred embodiment, the dosage form of the pharmaceutical composition includes (but is not limited to): injection solution, lyophilized powder injection.

In another preferred embodiment, the administration route of the pharmaceutical composition includes (but is not limited to): intravenous bolus injection, intravenous drip infusion, subcutaneous injection, intraperitoneal injection, intramuscular injection, and transdermal administration.

In another preferred embodiment, the pharmaceutical composition further comprises:
3) an anesthetically effective amount of a second compound.

In another preferred embodiment, the second compound is different from compound 1 or compound 10, and may be an existing anesthetic compound.

In another preferred embodiment, the second compound includes (but is not limited to): propofol, fentanyl, remifentanil, sufentanil, dexmedetomidine, etomidate, morphine, dezocine, pentazocine, oxycodone, ropivacaine, lidocaine, sevoflurane, or isoflurane.

(1) Compared with the prior art, the present invention has the following main advantages: The compound 1 and/or compound 10 have significant intravenous anesthesia activity;

(2) The compound 1 and/or compound 10 significantly reduce or basically have no side-effects such as limb jitters, head tilting, 16 pisthotonos in preclinical animal experiments;
(3) The compound 1 and/or compound 10 have the characteristics of good safety, rapid onset and/or rapid recovery, that is, having very excellent comprehensive performance;
(4) The compound 1 and/or compound 10 enhance the compliance of the medication, which is reflected in that the recovery of the number of autonomous activities and the rest time of the mice after multiple administrations of compound 1-2 are better than that of propofol.

The present invention will be further illustrated below with reference to the specific examples. It should be understood that these examples are only to illustrate the invention but not to limit the scope of the invention. The experimental methods with no specific conditions described in the following examples are generally performed under the conventional conditions, or according to the manufacture's instructions. Unless indicated otherwise, parts and percentage are calculated by weight.

Unless otherwise defined, all professional and scientific terminology used in the text have the same meanings as known to the skilled in the art. In addition, any methods and materials similar or equal with the record content can be applied to the methods of the invention. The method of the preferred embodiment described herein and the material are only for demonstration purposes.

Example 1

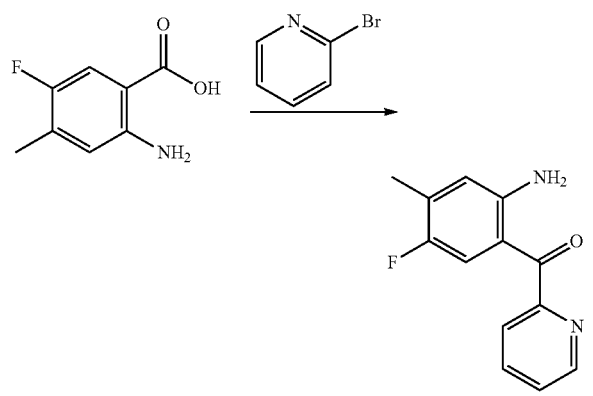

At −40° C., 8.2 ml (85.9 mmol, 4.4 eq) of 2-bromopyridine was added to a 250 ml three-necked flask containing 31.2 ml (78.1 mmol, 4.0 eq) of n-butyllithium (2.5M) and 50 ml of anhydrous ether, and then the react solution was stirred at −40° C. for 1 hour; a solution of 3.3 g (19.53 mmol, 1.0 eq) of 2-amino-5-fluoro-4-methylbenzoic acid in 40 ml of anhydrous tetrahydrofuran was added dropwise, warmed to 0° C., and reacted for 3 hours. TLC was used to monitor the progress of the reaction. After the reaction was completed, the reaction solution was poured into 200 ml of ice water, extracted with ethyl acetate (100 ml), dried over anhydrous sodium sulfate (50 g), filtered, and the filtrate was concentrated under reduced pressure (−0.08 MPa, 40° C.) to obtain an oily matter. The residue was purified by column (ethyl acetate:petroleum ether=1:20 to 1:6) to obtain 3.59 g of yellow solid compound 1-A, with a yield of 80%.

H NMR spectrum of the compound (deuterated methanol): δ 2.33 (CH3, s, 3H), 6.96 (CH, d, H), 7.58 (CH, m, H), 7.82 (CH, m, H), 7.94 (CH, m, H), 8.10 (CH, m, H), 8.75 (CH, m, H) ppm. MS: m/z: 231.09 (M+1).

Example 2

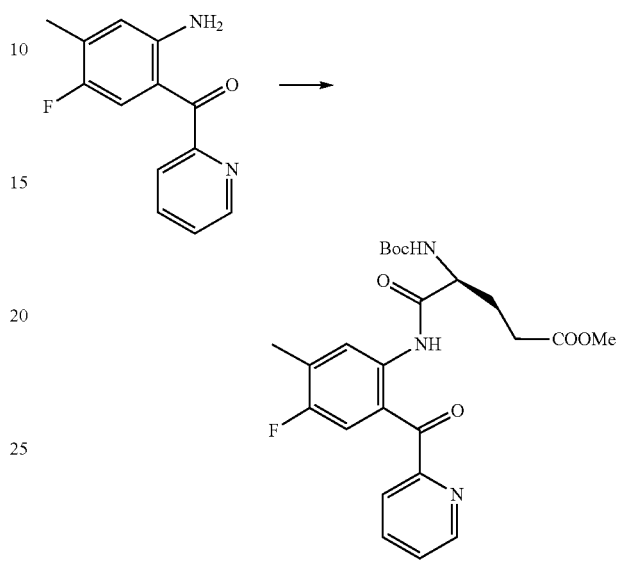

Compound 1-A (2.64 g, 11.5 mmol, 1.0 eq) and Boc-L-glutamate-5-methyl ester (3.3 g, 12.6 mmol, 1.1 eq) were weighed into a 100 ml three-necked bottle, and 30 ml of anhydrous dichloromethane was added, dissolved with stirring, and cooled to 0° C.; 10 ml of anhydrous dichloromethane solution containing dicyclohexylimine (2.37 g, 11.5 mmol, 1.0 eq) was added dropwise. After the addition, the temperature was raised to room temperature, reacted overnight. TLC was used to monitor the progress of the reaction. After the reaction was completed, filtered, the filter cake was washed with dichloromethane (2*10 ml), and the combined filtrate was purified by column (ethyl acetate:petroleum ether=1:20 to 1:3) to obtain 5.17 g yellow thick liquid compound 1-B, with a yield of 95%.

H NMR spectrum of the compound (deuterated methanol): δ 1.42 (3CH3, s, 9H), 2.28 (CH2, m, 2H), 2.33 (CH3, m, 3H), 2.35 (CH2, m, 2H), 3.61 (CH3, s, 3H), 4.60 (CH, t, H), 7.81 (CH, d, H), 7.82 (CH, m, H), 7.83 (CH, m, H), 7.94 (CH, m, H), 8.10 (CH, m, H), 8.75 (CH, m, H) ppm. MS: m/z: 474.20 (M+1).

Example 3

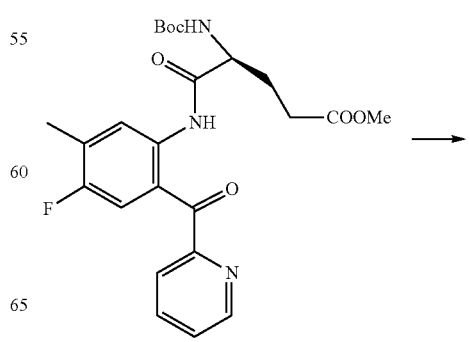

-continued

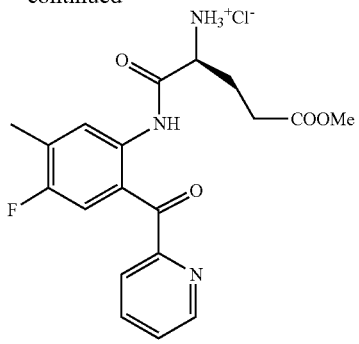

At room temperature, compound 1-B (5.6 g, 11.8 mmol, 1.0 eq) was dissolved in a 100 ml reaction flask containing 10 ml of methanol, and (17 ml, 47.4 mmol, 4.0 eq) homemade dioxane hydrochloride (2.8M) was slowly and continuously added, reacted at room temperature for 3 hours. The conversion of raw materials was complete, and the reaction solution (compound 1-C) was directly used in the next step.

H NMR spectrum of the compound (deuterated methanol): δ 2.33 (CH3, m, 3H), 2.35 (CH2, m, 2H), 2.76 (CH2, m, 2H), 3.61 (CH3, s, 3H), 4.58 (CH, m, H), 7.81 (CH, d, H), 7.82 (CH, m, H), 7.83 (CH, m, H), 7.94 (CH, m, H), 8.10 (CH, m, H), 8.31 (CH, m, H), 8.75 (CH, m, H) ppm. MS: m/z: 410.13 (M+1).

Example 4

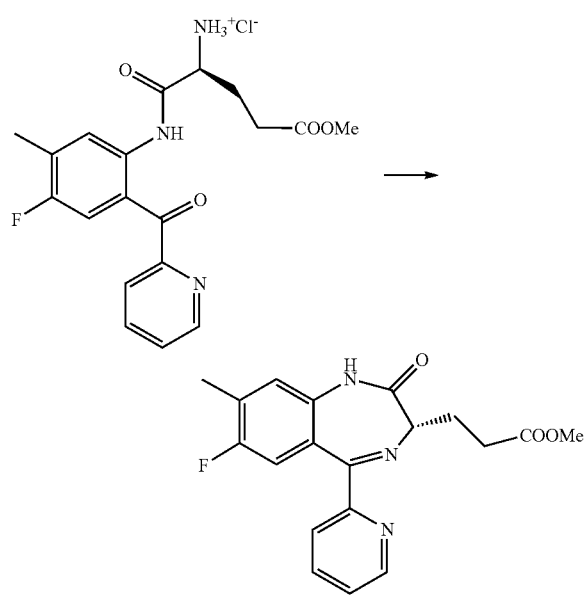

At room temperature, sodium bicarbonate (13.9 g, 165.2 mmol, 14.0 eq) was weighed into a 100 ml reaction flask, and 37 ml of acetonitrile (methanol:dioxane:acetonitrile=3:4:10) was added, and divided into 4 portions to be added into compound 1-C reaction solution (11.8 mmol, 1.0 eq) under rapid stirring, and reacted at room temperature for 3 hours, and the conversion was complete; the reaction solution was added with diatomaceous earth (5.0 g), filtrated and concentrated under reduced pressure (−0.08 MPa, 45° C.) to obtain a pale gray solid. Residual solid was purified by column (ethyl acetate:petroleum ether=1:10 to 2:1) to obtain 3.51 g of white solid compound 1-D with a yield of 83.8% in two steps.

H NMR spectrum of the compound (deuterated methanol): δ 2.33 (CH3, m, 3H), 2.35 (CH2, m, 2H), 2.38 (CH2, m, 2H), 3.61 (CH3, s, 3H), 4.14 (CH, m, H), 7.40 (CH, d, H), 7.74 (CH, m, H), 7.79 (CH, m, H), 7.79 (CH, m, H), 7.96 (CH, m, H), 8.71 (CH, m, H), 8.83 (CH, m, H) ppm. MS: m/z: 356.13 (M+1).

Example 5

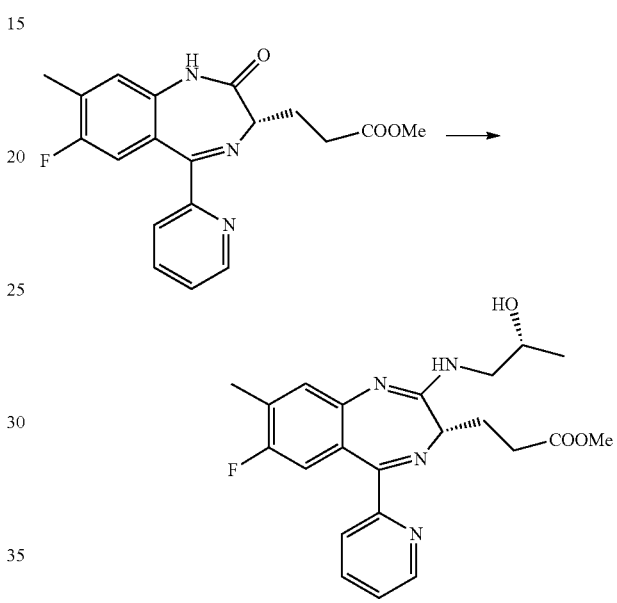

The raw material compound 1-D (3.5 g, 9.86 mmol, 1.0 eq) was weighed into a 100 ml three-necked bottle, added with 40 ml of anhydrous tetrahydrofuran, dissolved with stirring, cooled to −18° C., under argon protection; lithium diisopropylamide (4.9 ml, 9.86 mmol, 1.0 eq) was measured and slowly and continuously added to the reaction solution, during which the temperature was controlled between −10° C. and −5° C., and then reacted at 0° C. for 0.5 h; di-morpholinophosphoryl chloride (5.0 g, 19.72 mmol, 2.0 eq) was weighed and added to the reaction solution slowly and continuously in portions over 5 minutes, and the mixture was reacted between −5° C. and 0° C. for 1 hour; ®-1-amino-2-propanol (1.8 g, 24.06 mmol, 2.44eq) was weighed to a 50 ml single-necked bottle, added with 7 ml of anhydrous tetrahydrofuran, shaked to be even, and then slowly and continuously added to the reaction solution, during which the temperature was maintained between −2° C. and 4° C., for about 40 minutes; after the addition was completed, the reaction solution was warmed to room temperature, and carried out overnight; the reaction solution was poured into ice water to be quenched, extracted with ethyl acetate, and the organic phases were combined, dried over anhydrous sodium sulfate, filtered, concentrated under reduced pressure (−0.08 MPa, 42° C.), and the residue was purified by column (ethyl acetate:petroleum ether=1:10 to pure ethyl acetate) to obtain 3.05 g of orange-yellow oily matter compound 1-E, with a yield of 75%.

H NMR spectrum of the compound (deuterated methanol): δ 1.05 (CH3, d, 3H), 2.29 (CH2, m, 2H), 2.33 (CH3, m, 3H), 2.35 (CH2, m, 2H), 3.11 (CH, m, H), 3.61 (CH3, s, 3H), 3.69; 3.44 (CH2, m, 2H), 7.05 (CH, d, H), 7.74 (CH, m, H), 7.75 (CH, m, H), 7.79 (CH, m, H), 7.96 (CH, m, H), 8.71 (CH, m, H) ppm. MS: m/z: 413.19 (M+1).

Example 6

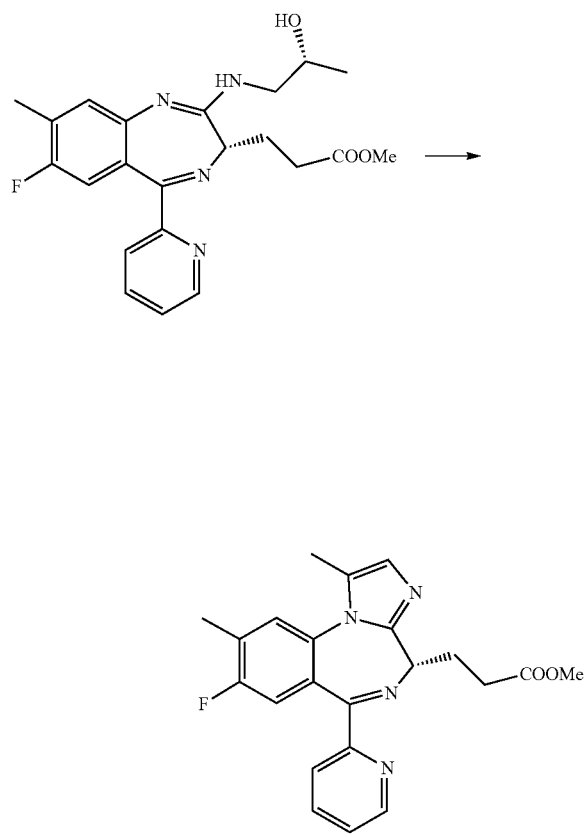

Compound 1-E (1.5 g, 3.64 mmol, 1.0 eq) was weighed and dissolved in 14 ml butanone, warmed to 30° C. Dess-Martin oxidant (5.41 g, 12.74 mmol, 3.5eq) was added in 4 portions, then warmed to 45° C. TLC was used to monitor the progress of the reaction until the conversion of raw materials was complete; the reaction solution was quenched with saturated sodium bicarbonate solution, extracted with ethyl acetate, dried over anhydrous sodium sulfate, filtered, and the filtrate was concentrated under reduced pressure (−0.08 MPa, 45° C.). The residue was purified by the column (ethyl acetate:petroleum ether=1:10 to pure ethyl acetate) to obtain 1.12 g of brown solid compound 1-F, with a yield of 78.7%.

H NMR spectrum of the compound (deuterated methanol): δ 2.23 (CH3, s, 3H), 2.33 (CH3, m, 3H), 2.33 (CH2, m, 2H), 2.35 (CH2, m, 2H), 3.61 (CH3, s, 3H), 4.32 (CH2, m, 2H), 7.31 (CH, m, H), 7.33 (CH, m, H), 7.69 (2CH, m, 2H), 7.74 (CH, m, H), 7.75 (CH, m, H), 7.79 (CH, m, H), 7.83 (CH, m, H), 7.89 (2CH, m, 2H), 7.96 (CH, m, H), 8.71 (CH, m, H)ppm. MS: m/z: 393.16 (M+1).

Example 7

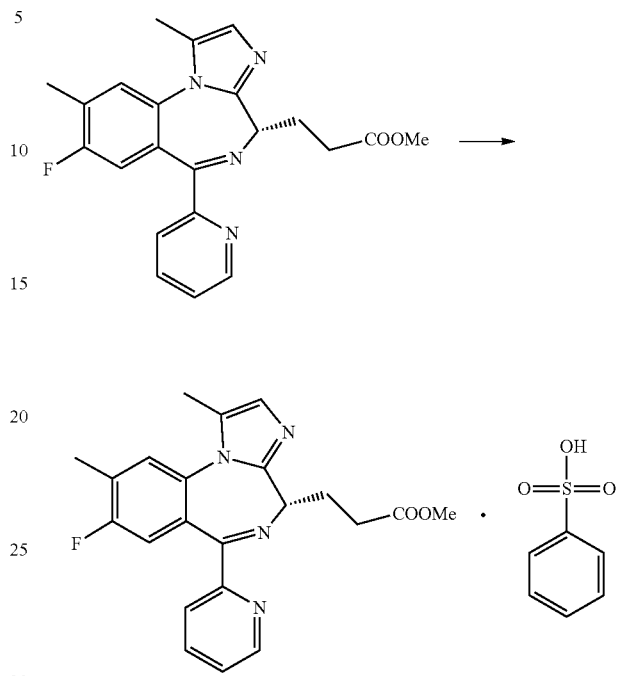

80 mL of anhydrous ether was added to a reaction bottle containing compound 1-F (0.25 g, 0.64 mmol, 1.0 eq), dissolved with stirring, cooled to 0° C., under argon protection; 1.5 ml of anhydrous ethyl acetate containing benzenesulfonic acid (0.1 g, 0.64 mmol, 1.0 eq) was added dropwise, reacted for 1 hour, and the solid was completely precipitated. The reaction was detected by TLC to be complete and filtered. The filter cake was vacuum dried (−0.09 MPa, 20° C.) to obtain 0.31 g of off-white solid compound 1-1, with a yield of 88.9%.

H NMR spectrum of the compound (deuterated methanol): δ 2.23 (CH3, s, 3H), 2.33 (CH3, m, 3H), 2.33 (CH2, m, 2H), 2.35 (CH2, m, 2H), 3.61 (CH3, s, 3H), 4.32 (CH, m, H), 7.31 (CH, m, H), 7.33 (CH, m, H), 7.69 (2CH, m, 2H), 7.74 (CH, m, H), 7.75 (CH, m, H), 7.79 (CH, m, H), 7.83 (CH, m, H), 7.89 (2CH, m, 2H), 7.96 (CH, m, H), 8.71 (CH, m, H)ppm. MS: m/z: 551.17 (M+1).

Example 8

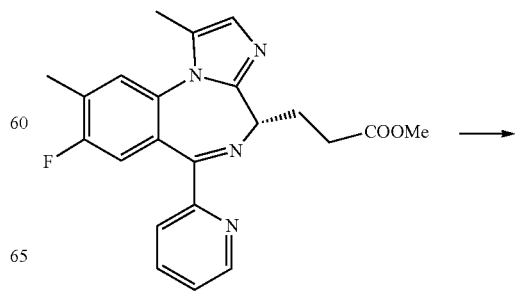

-continued

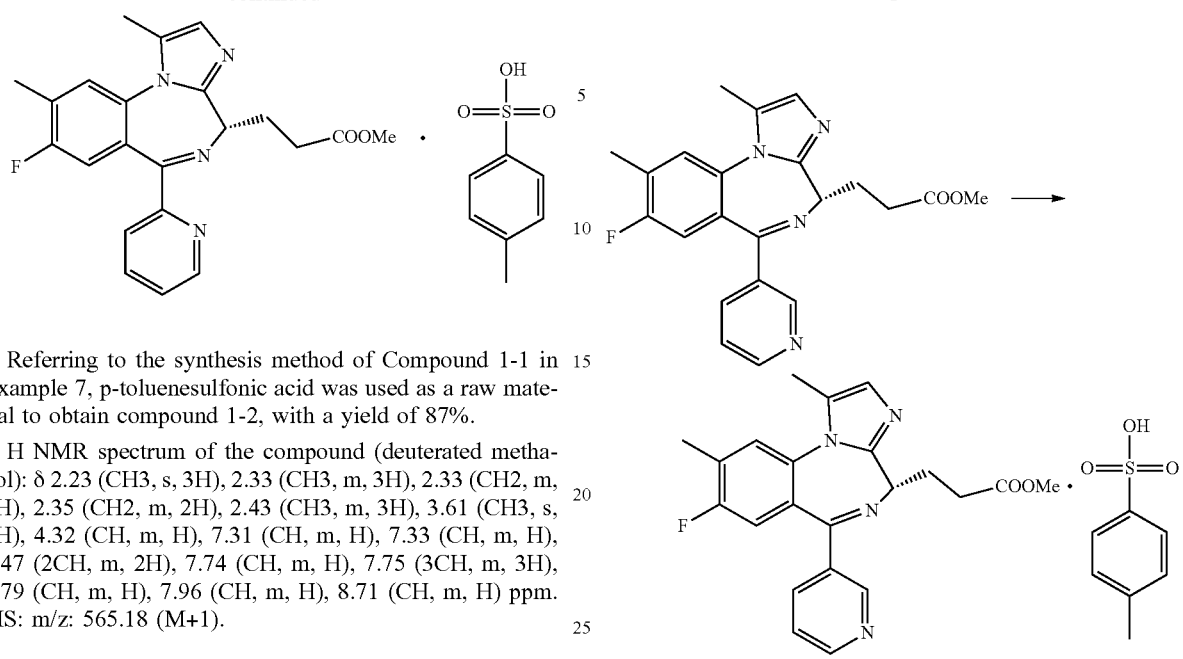

Example 10

Referring to the synthesis method of Compound 1-1 in Example 7, p-toluenesulfonic acid was used as a raw material to obtain compound 1-2, with a yield of 87%.

H NMR spectrum of the compound (deuterated methanol): δ 2.23 (CH3, s, 3H), 2.33 (CH3, m, 3H), 2.33 (CH2, m, 2H), 2.35 (CH2, m, 2H), 2.43 (CH3, m, 3H), 3.61 (CH3, s, 3H), 4.32 (CH, m, H), 7.31 (CH, m, H), 7.33 (CH, m, H), 7.47 (2CH, m, 2H), 7.74 (CH, m, H), 7.75 (3CH, m, 3H), 7.79 (CH, m, H), 7.96 (CH, m, H), 8.71 (CH, m, H) ppm. MS: m/z: 565.18 (M+1).

Example 9

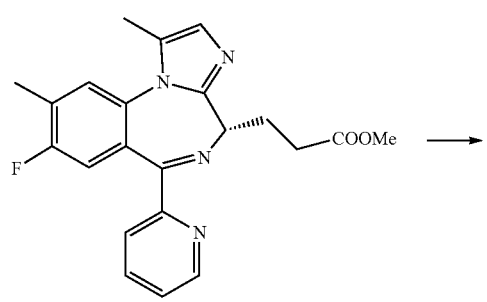

Referring to the synthesis method of compound 1-1 in Example 7, hydrochloric acid was used as a raw material to obtain compound 1-3, with a yield of 92%.

H NMR spectrum of the compound (deuterated methanol): δ 2.23 (CH3, s, 3H), 2.33 (CH3, m, 3H), 2.33 (CH2, m, 2H), 2.35 (CH2, m, 2H), 3.61 (CH3, s, 3H), 4.32 (CH, m, H), 7.31 (CH, m, H), 7.33 (CH, m, H), 7.74 (CH, m, H), 7.75 (CH, m, H), 7.79 (CH, m, H), 7.96 (CH, m, H), 8.71 (CH, m, H) ppm. MS: m/z: 429.14 (M+1).

Referring to the synthesis method of compound 1-1 in Example 7, 3-bromopyridine and p-toluenesulfonic acid were used as raw materials to obtain compound 1-4 with a yield of 85.3%.

H NMR spectrum of the compound (deuterated methanol): δ 2.23 (CH3, s, 3H), 2.33 (CH3, m, 3H), 2.33 (CH2, m, 2H), 2.35 (CH2, m, 2H), 2.43 (CH3, m, 3H), 3.61 (CH3, s, 3H), 4.32 (CH, m, H), 7.31 (CH, m, H), 7.33 (CH, m, H), 7.47 (2CH, m, 2H), 7.58 (CH, m, H), 7.75 (3CH, m, 3H), 8.30 (CH, m, H), 8.75 (CH, m, H), 9.07 (CH, m, H) ppm. MS: m/z: 565.18 (M+1).

Example 11

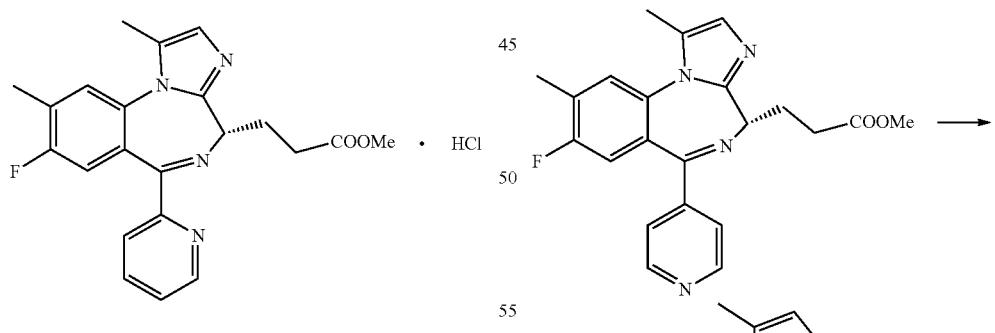

Referring to the synthesis method of compound 1-1 in Example 7, 4-bromopyridine and p-toluenesulfonic acid were used as raw materials to obtain compound 1-5 with a yield of 86%.

H NMR spectrum of the compound (deuterated methanol): δ 2.23 (CH3, s, 3H), 2.33 (CH3, m, 3H), 2.33 (CH2, m, 2H), 2.35 (CH2, m, 2H), 2.43 (CH3, m, 3H), 3.61 (CH3, s, 3H), 4.32 (CH, m, H), 7.31 (CH, m, H), 7.33 (CH, m, H), 7.47 (2CH, m, 2H), 7.75 (3CH, m, 3H), 7.98 (2CH, m, 2H), 8.64 (2CH, m, 2H) ppm. MS: m/z: 565.18 (M+1).

Example 12

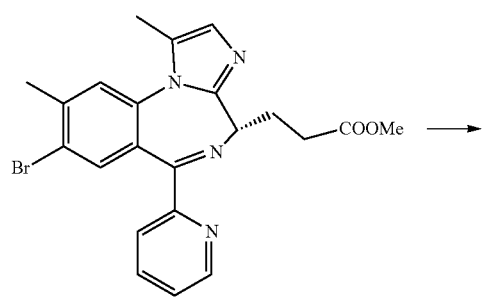

Referring to the synthesis method of compound 1-1 in Example 7, 2-amino-5-bromo-4-methylbenzoic acid and p-toluenesulfonic acid were used as raw materials to obtain compound 1-6 with a yield of 84.5%.

H NMR spectrum of the compound (deuterated methanol): δ 2.23 (CH3, s, 3H), 2.33 (CH3, m, 3H), 2.33 (CH2, m, 2H), 2.35 (CH2, m, 2H), 2.43 (CH3, m, 3H), 3.61 (CH3, s, 3H), 4.32 (CH, m, H), 7.24 (CH, m, H), 7.31 (CH, m, H), 7.47 (2CH, m, 2H), 7.75 (2CH, m, 2H), 7.74 (CH, m, H), 7.79 (CH, m, H), 7.86 (CH, m, H), 7.96 (CH, m, H), 8.71 (CH, m, H) ppm. MS: m/z: 625.10 (M+1).

Example 13

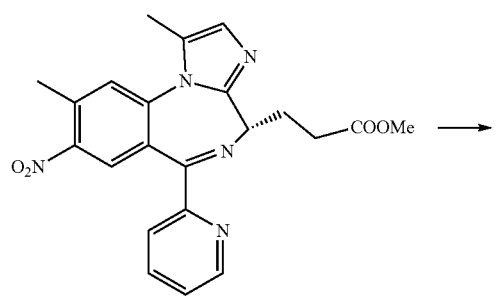

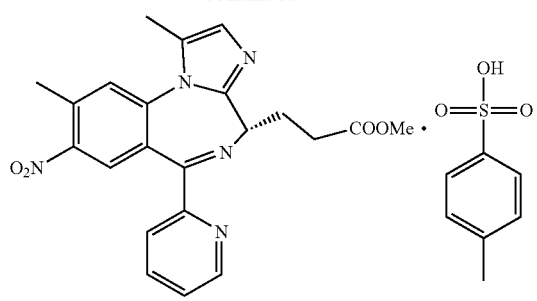

Referring to the synthesis method of compound 1-1 in Example 7, 2-amino-5-nitro-4-methylbenzoic acid and p-toluenesulfonic acid were used as raw materials to obtain compound 1-7 with a yield of 83%.

H NMR spectrum of the compound (deuterated methanol): δ 2.23 (CH3, s, 3H), 2.33 (CH2, m, 2H), 2.34 (CH3, m, 3H), 2.35 (CH2, m, 2H), 2.43 (CH3, m, 3H), 3.61 (CH3, s, 3H), 4.32 (CH, m, H), 7.31 (CH, m, H), 7.47 (2CH, m, 2H), 7.75 (2CH, m, 2H), 7.61 (CH, m, H), 7.74 (CH, m, H), 7.79 (CH, m, H), 7.96 (CH, m, H), 8.47 (CH, m, H), 8.71 (CH, m, H) ppm. MS: m/z: 592.18 (M+1).

Example 14

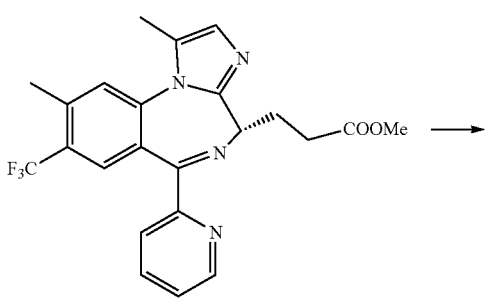

Referring to the synthesis method of compound 1-1 in Example 7, 2-amino-5-trifluoromethyl-4-methylbenzoic acid and p-toluenesulfonic acid were used as raw materials to obtain compound 1-8 with a yield of 84.7%.

H NMR spectrum of the compound (deuterated methanol): δ 2.23 (CH3, s, 3H), 2.29 (CH3, m, 3H), 2.33 (CH2, m, 2H), 2.35 (CH2, m, 2H), 2.43 (CH3, m, 3H), 3.61 (CH3, s, 3H), 4.32 (CH, m, H), 7.28 (CH, m, H), 7.31 (CH, m, H), 7.47 (2CH, m, 2H), 7.75 (2CH, m, 2H), 7.74 (CH, m, H), 7.79 (CH, m, H), 7.96 (CH, m, H), 8.00 (CH, m, H), 8.71 (CH, m, H) ppm. MS: m/z: 615.18 (M+1).

Example 15

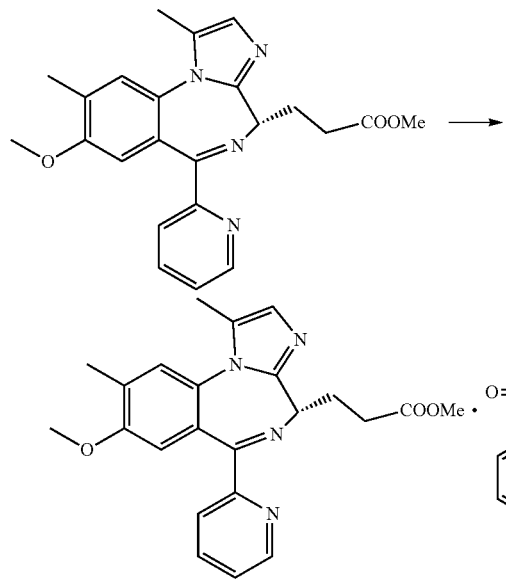

Referring to the synthesis method of compound 1-1 in Example 7, 2-amino-5-methoxy-4-methylbenzoic acid and p-toluenesulfonic acid were used as raw materials to obtain compound 1-9 with a yield of 82.9%.

H NMR spectrum of the compound (deuterated methanol): δ 2.15 (CH3, s, 3H), 2.23 (CH3, s, 3H), 2.33 (CH2, m, 2H), 2.35 (CH2, m, 2H), 2.43 (CH3, m, 3H), 3.61 (CH3, s, 3H), 3.72 (CH3, s, 3H), 4.32 (CH, m, H), 7.31 (CH, d, H), 7.35 (2CH, d, 2H), 7.47 (2CH, d, 2H), 7.74 (CH, m, H), 7.75 (2CH, m, 2H), 7.79 (CH, m, H), 7.96 (CH, m, H), 8.71 (CH, m, H) ppm. MS: m/z: 577.20 (M+1).

Example 16

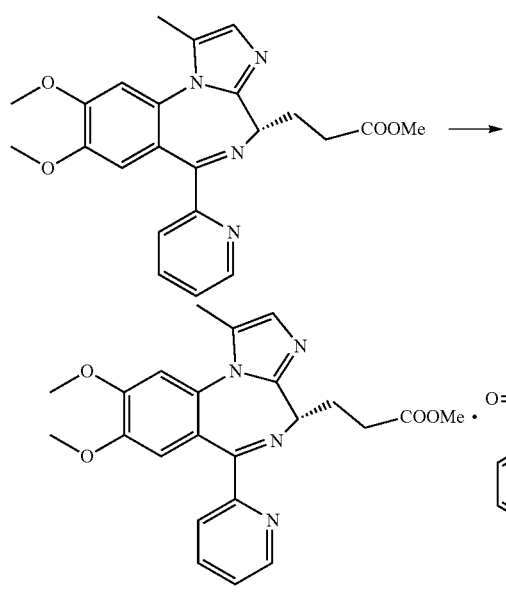

Referring to the synthesis method of compound 1-1 in Example 7, 2-amino-4,5-dimethoxybenzoic acid and p-toluenesulfonic acid were used as raw materials to obtain compound 1-10 with a yield of 81.4%.

H NMR spectrum of the compound (deuterated methanol): δ 2.23 (CH3, s, 3H), 2.33 (CH2, m, 2H), 2.35 (CH2, m, 2H), 2.43 (CH3, s, 3H), 3.61 (CH3, s, 3H), 3.85 (2CH3, d, 6H), 4.32 (CH, m, H), 7.09 (CH, s, H), 7.31 (CH, s, H), 7.40 (CH, s, H), 7.47 (2CH, d, 2H), 7.75 (2CH, m, 2H), 7.79 (CH, m, H), 7.96 (CH, m, H), 8.71 (CH, m, H) ppm. MS: m/z: 593.20 (M+1).

Example 17

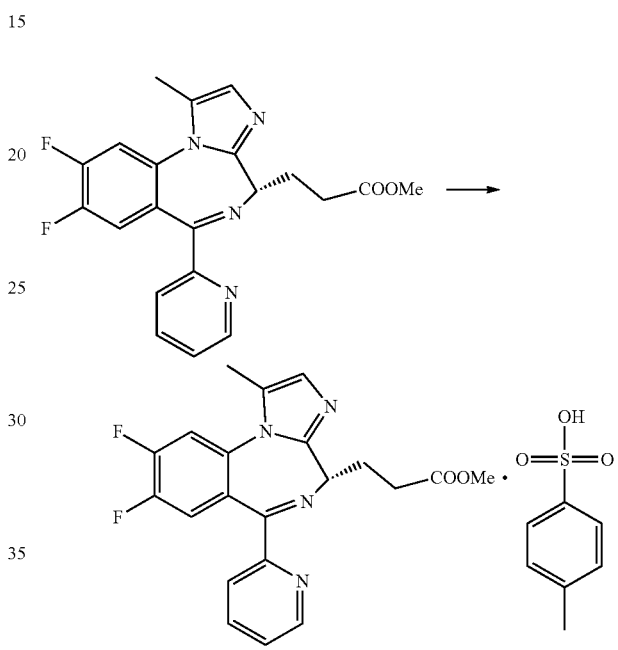

Referring to the synthesis method of compound 1-1 in Example 7, 2-amino-4,5-difluorobenzoic acid and p-toluenesulfonic acid were used as raw materials to obtain compound 1-11 with a yield of 84.2%.

H NMR spectrum of the compound (deuterated methanol): δ 2.23 (CH3, s, 3H), 2.33 (CH2, m, 2H), 2.35 (CH2, m, 2H), 2.43 (CH3, s, 3H), 3.61 (CH3, s, 3H), 4.32 (CH, m, H), 7.16 (CH, m, H), 7.31 (CH, s, H), 7.47 (2CH, d, 2H), 7.75 (2CH, m, 2H), 7.78 (CH, m, H), 7.79 (CH, m, H), 7.96 (CH, m, H), 8.71 (CH, m, H) ppm. MS: m/z: 569.16 (M+1).

Example 18

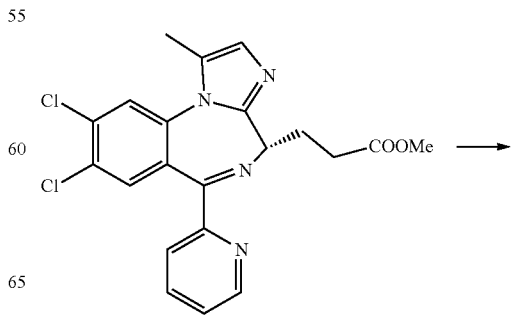

-continued

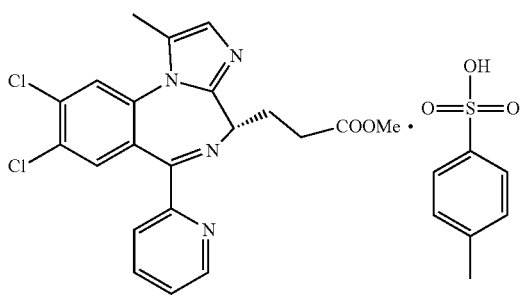

Referring to the synthesis method of compound 1-1 in Example 7, 2-amino-4,5-dichlorobenzoic acid and p-toluenesulfonic acid were used as raw materials to obtain compound 1-12 with a yield of 84.8%.

H NMR spectrum of the compound (deuterated methanol): δ 2.23 (CH3, s, 3H), 2.33 (CH2, m, 2H), 2.35 (CH2, m, 2H), 2.43 (CH3, s, 3H), 3.61 (CH3, s, 3H), 4.32 (CH, m, H), 7.31 (CH, s, H), 7.42 (CH, s, H), 7.47 (2CH, d, 2H), 7.74 (CH, d, H), 7.75 (2CH, m, 2H), 7.79 (CH, m, H), 7.85 (CH, m, H), 7.96 (CH, m, H), 8.71 (CH, m, H) ppm. MS: m/z: 601.10 (M+1).

Example 19

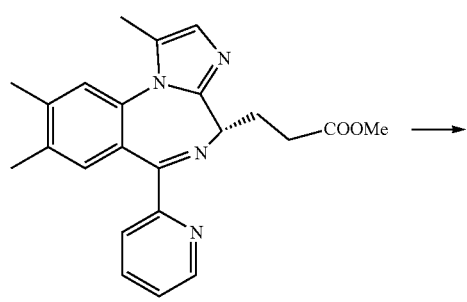

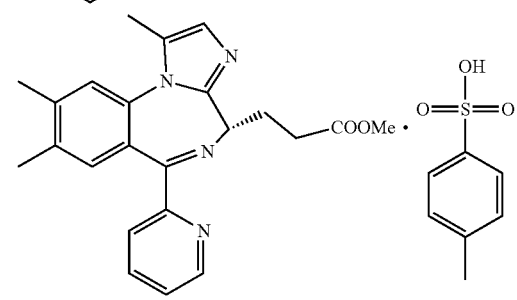

Referring to the synthesis method of compound 1-1 in Example 7, 2-amino-4,5-dimethylbenzoic acid and p-toluenesulfonic acid were used as raw materials to obtain compound 1-13 with a yield of 86%.

H NMR spectrum of the compound (deuterated methanol): δ 2.23 (CH3, s, 3H), 2.31 (CH3, m, 3H), 2.33 (CH2, m, 2H), 2.35 (CH2, m, 2H), 2.43 (CH3, s, 3H), 2.47 (CH3, s, 3H), 3.61 (CH3, s, 3H), 4.32 (CH, m, H), 7.30 (CH, d, H), 7.31 (CH, d, H), 7.47 (2CH, d, 2H), 7.69 (CH, m, H), 7.74 (CH, m, H), 7.75 (2CH, m, 2H), 7.79 (CH, m, H), 7.96 (CH, m, H), 8.71 (CH, m, H) ppm. MS: m/z: 561.21 (M+1).

Example 20

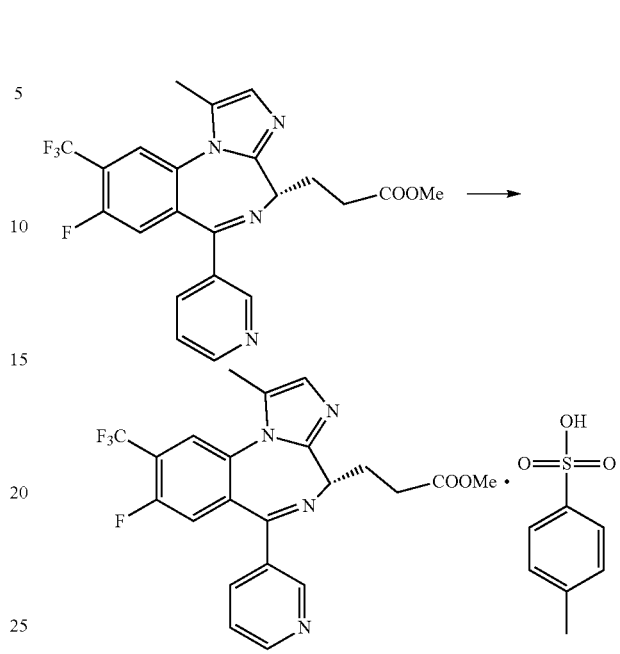

Referring to the synthesis method of compound 1-1 in Example 7, 3-bromopyridine, 2-amino-5-fluoro-4-(trifluoromethyl)benzoic acid and p-toluenesulfonic acid were used as raw materials to obtain compound 1-14 with a yield of 82.5%.

H NMR spectrum of the compound (deuterated methanol): δ 2.23 (CH3, s, 3H), 2.33 (CH2, m, 2H), 2.35 (CH2, m, 2H), 2.43 (CH3, s, 3H), 3.61 (CH3, s, 3H), 4.32 (CH, m, H), 7.31 (CH, s, H), 7.47 (2CH, d, 2H), 7.58 (CH, m, H), 7.64 (CH, m, H), 7.73 (CH, m, H), 7.75 (2CH, m, 2H), 8.30 (CH, m, H), 8.75 (CH, m, H), 9.07 (CH, m, H) ppm. MS: m/z: 619.16 (M+1).

Example 21

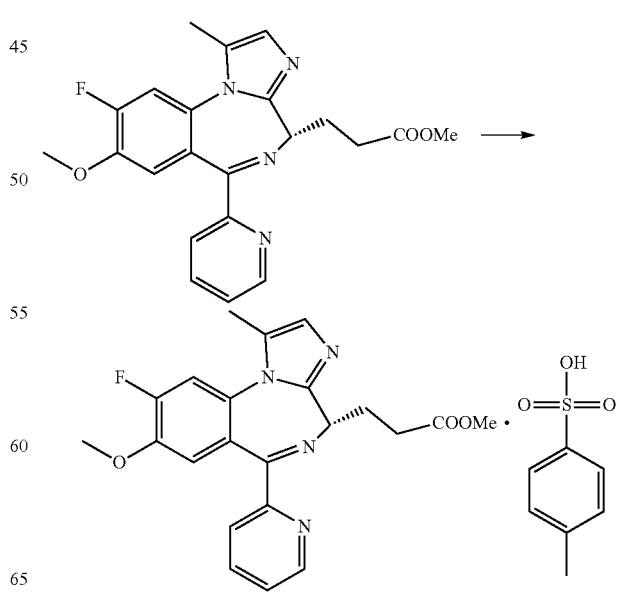

Referring to the synthesis method of compound 1-1 in Example 7, 4-fluoro-5-methoxybenzoic acid and p-toluenesulfonic acid were used as raw materials to obtain compound 1-15 with a yield of 83.6%.

H NMR spectrum of the compound (deuterated methanol): δ 2.23 (CH3, s, 3H), 2.33 (CH2, m, 2H), 2.35 (CH2, m, 2H), 2.43 (CH3, s, 3H), 3.61 (CH3, s, 3H), 3.83 (CH3, s, 3H), 4.32 (CH, m, H), 7.18 (CH, s, H), 7.31 (CH, s, H), 7.38 (CH, s, H), 7.47 (2CH, d, 2H), 7.74 (CH, m, H), 7.75 (2CH, m, 2H), 7.79 (CH, m, H), 7.96 (CH, m, H), 8.71 (CH, m, H)ppm. MS: m/z: 581.18 (M+1).

Example 22

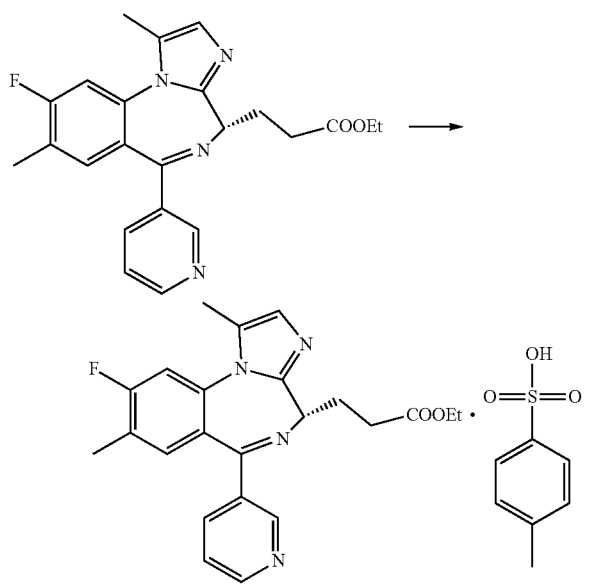

Referring to the synthesis method of compound 1-1 in Example 7, 3-bromopyridine, Boc-L-glutamate-5-ethyl ester, 2-amino-4-fluoro-5-methylbenzoic acid and p-toluenesulfonic acid were used as raw materials to obtain compound 1-16 with a yield of 87.3%.

H NMR spectrum of the compound (deuterated methanol): 61.07 (CH3, s, 3H), 2.23 (CH3, s, 3H), 2.23 (CH3, s, 3H), 2.33 (CH2, m, 2H), 2.35 (CH2, m, 2H), 2.43 (CH3, s, 3H), 4.01 (CH2, s, 2H), 4.32 (CH, m, H), 7.13 (CH, d, H), 7.31 (CH, s, H), 7.47 (2CH, m, 2H), 7.58 (CH, t, H), 7.72 (CH, m, H), 7.75 (2CH, m, 2H), 8.30 (CH, m, H), 8.75 (CH, m, H), 9.07 (CH, m, H) ppm. MS: m/z: 579.20 (M+1).

Example 23

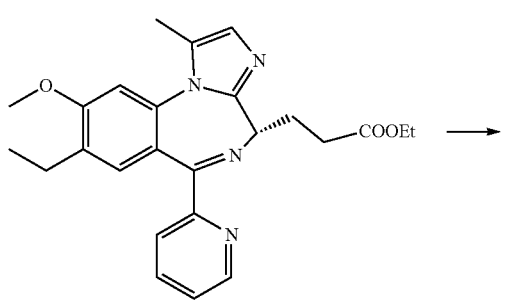

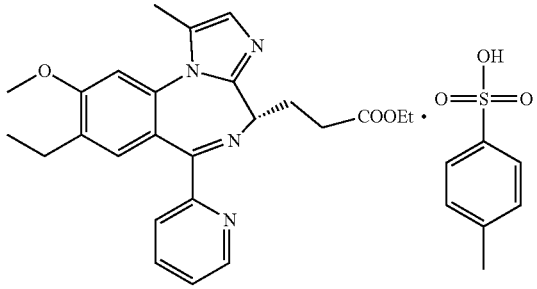

Referring to the synthesis method of compound 1-1 in Example 7, Boc-L-glutamate-5-ethyl ester, 2-amino-4-methoxy-5-ethylbenzoic acid and p-toluenesulfonic acid were used as raw materials to obtain compound 1-17, with a yield of 81.5%.

H NMR spectrum of the compound (deuterated methanol): δ 1.07 (CH3, m, 3H), 1.12 (CH3, m, 3H), 2.23 (CH3, s, 3H), 2.33 (CH2, m, 2H), 2.35 (CH2, m, 2H), 2.43 (CH3, m, 3H), 2.50 (CH2, m, 2H), 3.72 (CH3, s, 3H), 4.01 (CH2, m, 2H), 4.32 (CH, m, H), 7.09 (CH, s, H), 7.31 (CH, s, H), 7.47 (2CH, d, 2H), 7.74 (CH, m, H), 7.75 (2CH, m, 2H), 7.78 (CH, m, H), 7.79 (CH, m, H), 7.96 (CH, m, H), 8.71 (CH, m, H) ppm. MS: m/z: 605.24 (M+1).

Pharmacological Activity and Safety Assessment

During surgery and diagnostic operations, it is necessary to have a good control of the effect of the anesthetic drug, so as to ensure the smooth operation of the surgery, and to end the anesthesia as soon as possible after the operation is completed. Good intravenous anesthetic drugs should meet the requirements of rapid onset, rapid recovery, and good safety.

Example 24 Experiments of Disappearance of Righting Reflex in Mice Induced by Drugs After ICR mice (male, 18-25 g) were fast injected with the same dose (100 mg/kg) of the test drug in a single bolus via the tail vein, the incubation period and the duration of disappearance of the righting reflex in mice were recorded. Wherein, the incubation period refers to the time from the start of administration to the disappearance of the animal's righting reflex, and the duration refers to the time from the disappearance of the righting reflex to the recovery. The experimental results are shown in the table below.

TABLE 1

Experimental results of disappearance of righting reflex in mice

| Compound | Incubation period (min) | Duration (min) |
|---|---|---|
| Remimazolam (p-toluenesulfonate) | 0.73 | 9.43 |
| Remimazolam (besylate) | 0.64 | 10.61 |
| 1-1 | 0.35 | 7.00 |
| 1-2 | 0.52 | 6.02 |
| 1-3 | 0.30 | 7.20 |
| 1-4 | 0.37 | 9.32 |
| 1-5 | 0.40 | 8.21 |
| 1-6 | 0.47 | 7.98 |
| 1-7 | 0.60 | 8.39 |
| 1-8 | 0.55 | 8.60 |
| 1-9 | 0.63 | 8.77 |
| 1-10 | 0.48 | 7.86 |

TABLE 1-continued

Experimental results of disappearance of righting reflex in mice

| Compound | Incubation period (min) | Duration (min) |
|---|---|---|
| 1-11 | 0.53 | 7.28 |
| 1-12 | 0.42 | 8.35 |
| 1-14 | 0.58 | 6.30 |
| 1-15 | 0.54 | 9.02 |
| 1-16 | 0.86 | 9.35 |
| 1-17 | 0.75 | 7.24 |

It can be seen from Table 1 that the anesthetic effect of the compound of the present invention is comparable to or better than that of remimazolam p-toluenesulfonate or remimazolam besylate.

Further, compared with remimazolam p-toluenesulfonate or remimazolam besylate, most of the compounds of the present invention have the advantages of faster onset and faster recovery.

Example 25 Experiments of Effective Dose and Lethal Dose of Intravenous Administration in Mice ICR mice (males, 18-25 g) were randomly grouped and were fast given a single bolus of different doses of test drug via the tail vein, and the lowest dose causing the righting reflex to disappear (effective dose) and the dose causing animal death (lethal dose) were recorded, and the treatment windows (lethal dose/effective dose) were calculated.

TABLE 2

Effective and lethal dose of different test compounds

| Compound | Effective dose (mg/kg) | Lethal dose (mg/kg) | Treatment window |
|---|---|---|---|
| Remimazolam (p-toluenesulfonate) | 60 | 220 | 3.6 |
| Remimazolam (besylate) | 60 | 280 | 4.6 |
| 1-1 | 60 | 320 | 5.3 |
| 1-2 | 40 | 360 | 9 |
| 1-3 | 60 | 280 | 4.67 |
| 1-4 | 80 | 280 | 3.5 |
| 1-5 | 60 | 320 | 5.3 |
| 1-6 | 100 | 380 | 3.8 |
| 1-7 | 40 | 240 | 6 |
| 1-8 | 40 | 260 | 6.5 |
| 1-9 | 60 | 260 | 4.3 |
| 1-10 | 80 | 300 | 3.75 |
| 1-11 | 80 | 320 | 4 |
| 1-12 | 60 | 300 | 5 |
| 1-13 | 80 | 320 | 4 |
| 1-14 | 100 | 360 | 3.6 |
| 1-15 | 60 | 320 | 5.3 |
| 1-16 | 40 | 280 | 7 |
| 1-17 | 80 | 360 | 4.5 |

The data in Table 2 above shows that in the mouse test, the safety windows of the compounds of the present invention were significantly wider, and the anesthesia processes were stable. No adverse effects such as limb jitters, convulsions and opisthotonus were observed, and they had good safety.

Typically, compared to remimazolam (p-toluenesulfonate), compound 1-2, taken as an example, had the effective dose reduced by 33.3%, and the lethal dose was increased by 64%, and the treatment window was increased by 2.5 times.

Therefore, the present invention provides a compound for anesthesia with a combination of rapid onset, rapid recovery, good safety and minimal side effects.

Example 26 Effect of Multiple (9 Times) i.v. Administrations of Compound 1-2 on the Duration of Disappearance of Righting Reflex in Mice

Experimental Method

Animals in each group were given the corresponding drug solution multiple times by the tail vein injection (i.v.) in accordance with the corresponding group, 0.1 ml per mouse each time, for 9 times of consecutive injections (the administration group mice were injected when the righting reflex was recovered). The durations of each disappearance of righting reflex were recorded, and the data was expressed as an average.

Experimental Result

After intravenous injection of compound 1-2, the duration of the righting reflex disappearance of mice was dose-dependent. At the same time, the duration of the righting reflex disappearance of mice rapidly increased with the increase of the number of administrations in each dose group. After repeated administrations for 5-6 times, steady state was reached. After a single administration, the duration of righting reflex disappearance in the 75 mg/kg dose group of compound 1-2 is close to that in propofol group (Table 3), but after 6-7 administrations, the disappearance time of righting reflex in 75 mg/kg dose group of compound 1-2 is 65-70% of that of the mice in the propofol group, see Table 3 and Table 4.

TABLE 3

Effect of multiple i.v. administrations of compound 1-2 on the duration of righting reflex disappearance

| Group | dose | righting reflex disappearance time (min) | | | | | | | | |
|---|---|---|---|---|---|---|---|---|---|---|
| | | 1 | 2 | 3 | 4 | 5 | 6 | 7 | 8 | 9 |
| blank | N.S | 0.0 | 0.0 | 0.0 | 0.0 | 0.0 | 0.0 | 0.0 | 0.0 | 0.0 |
| Propofol | 20 mg/kg | 4.0 | 5.8 | 10.4 | 12.1 | 11.7 | 15.2 | 17.6 | 16.2 | 17.1 |
| Compound 1-2 | 100 mg/kg | 8.9 | 10.8 | 13.8 | 15.8 | 16.2 | 21.5 | 20.9 | 21.2 | 21.1 |
| | 75 mg/kg | 5.3 | 6.7 | 8.4 | 9.1 | 10.2 | 11.5 | 12.1 | 11.1 | 11.1 |
| | 50 mg/kg | 2.5 | 4.4 | 4.8 | 5.6 | 5.9 | 5.2 | 6.6 | 6.5 | 6.6 |

TABLE 4

Effect of multiple i.v. administrations of compound 1-2 on the duration of righting reflex disappearance

| Group | dose | Percentage of extension of righting reflex disappearance (%) | | | | | | | | |
|---|---|---|---|---|---|---|---|---|---|---|
| | | 1 | 2 | 3 | 4 | 5 | 6 | 7 | 8 | 9 |
| blank | N.S | 100 | 100 | 100 | 100 | 100 | 100 | 100 | 100 | 100 |
| Propofol | 20 mg/kg | 100 | 144 | 259 | 300 | 292 | 378 | 439 | 404 | 426 |
| Compound 1-2 | 100 mg/kg | 100 | 121 | 154 | 177 | 181 | 240 | 234 | 238 | 236 |
| | 75 mg/kg | 100 | 128 | 159 | 173 | 194 | 219 | 231 | 211 | 211 |
| | 50 mg/kg | 100 | 179 | 192 | 227 | 237 | 208 | 268 | 260 | 268 |

It can be seen from Tables 3 and 4 that: both Propofol and the test drug compound 1-2 multiple i.v. administrations prolonged the duration of righting reflex in mice, and the duration of righting reflex disappearance of mice in both propofol group and the test drug group with different doses reached steady state after 6-7 consecutive administrations. However, the prolonged rate of righting reflex disappearance time after multiple administrations of compound 1-2 in each dose group were significantly lower than that in propofol group, indicating that the accumulation effect of compound 1-2 is lower than that of propofol, suggesting the safety of compound 1-2 is better.

Example 27 Effect of Compound 1-2 Single and Multiple (10 Times) I.V. Administrations on the Autonomous Activity of Mice Experimental Method Single Administration Animals in each group were tested for their autonomous activities, each mouse for 10 minutes. After that, the animals in each group were given a single corresponding drug solution by the tail vein injection (i.v.) according to the corresponding group, 0.1 ml per 10 g body weight, and the autonomous activity of the mice was measured immediately after the administration, and the recording time was 50 min. Data were expressed as mean±standard deviation. Wherein, the dosage of propofol was 20 mg/kg.

Multiple Administration

Animals in each group were given the corresponding drug solution multiple times by the tail vein injection (i.v.) in accordance with the corresponding group, 0.1 ml per mouse each time, for ten times of consecutive injections (the administration group mice were injected when the righting reflex was recovered). Then the autonomous activity of mice was measured immediately and the recording time was 50 minutes. Data were expressed as mean±standard deviation.

Experimental Result

Figure 2:
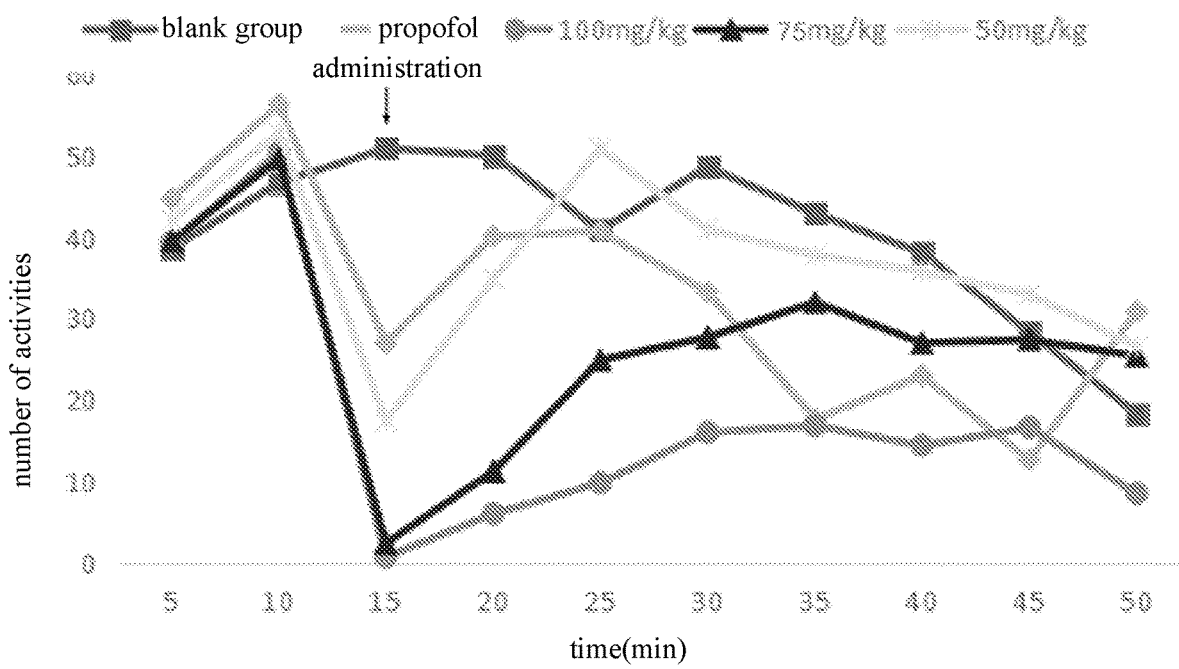
FIG. 2 shows the effect of a single administration of compound 1-2 in Example 27 on the number of mice's autonomous activities.
Figure 3:
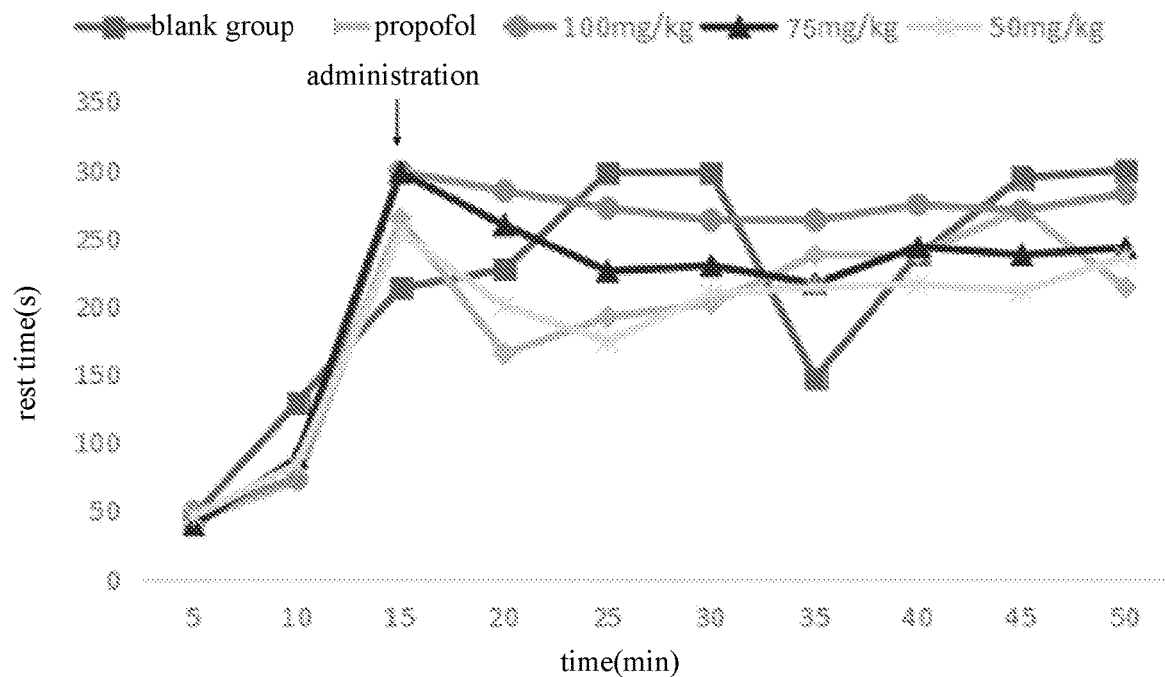
FIG. 3 shows the effect of a single administration of compound 1-2 in Example 27 on the rest time between mice's autonomous activities.

1. Effect of Single Administration of Compound 1-2 on the Autonomous Activity of Mice There was no difference in the autonomous activity of the mice in each group before administration, and the autonomous activity of the blank group mice decreased slowly with the extension of the exploration time. In the single-positive drug propofol group, the autonomic activity was significantly reduced at 5 minutes after injection, and the mice in this group were awake 5-10 minutes after administration, and their autonomic activities basically recovered after 15 minutes of administration, but the subsequent autonomy activities regardless of the total distance and the number of activities were lower than those of the blank control group. After a single injection of different doses of compound 1-2 in mice, the autonomous activity of the mice was determined. The results showed that within 10 minutes of injection, the total distance of the autonomous activity of mice in the 50 mg/kg-100 mg/kg dose group was significantly lower than that of the blank group at the same time and showed to be dose-dependent. In the low-dose group of compound 1-2 (50 mg/kg), after the mice had been administrated for 15 minutes, the autonomous activity returned to normal level; in the medium-dose group of compound 1-2 (75 mg/kg), after the mice had been administrated for 35 minutes, the autonomous activity returned to normal level; in the high-dose group of compound 1-2 (100 mg/kg), the autonomous activity was consistently lower than that of the blank group during the test period, see FIG. 1-3.

Figure 4:
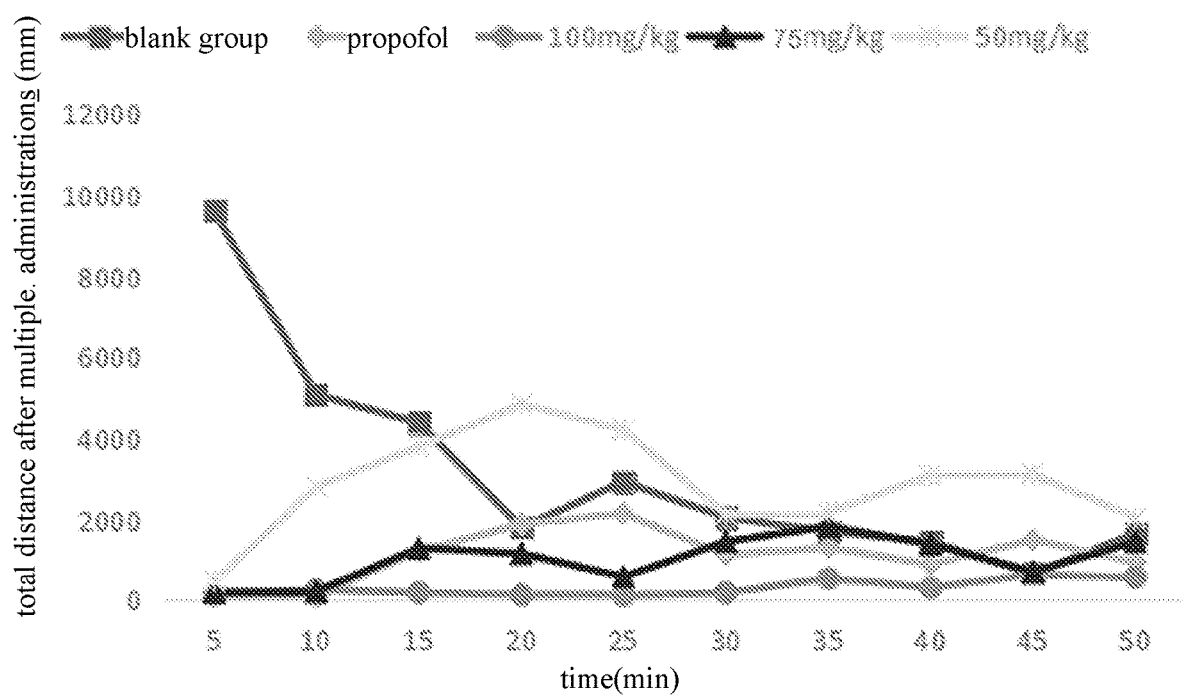
FIG. 4 shows the effect of multiple administrations of compound 1-2 in Example 27 on the total distance of mice's autonomous activities.
Figure 5:
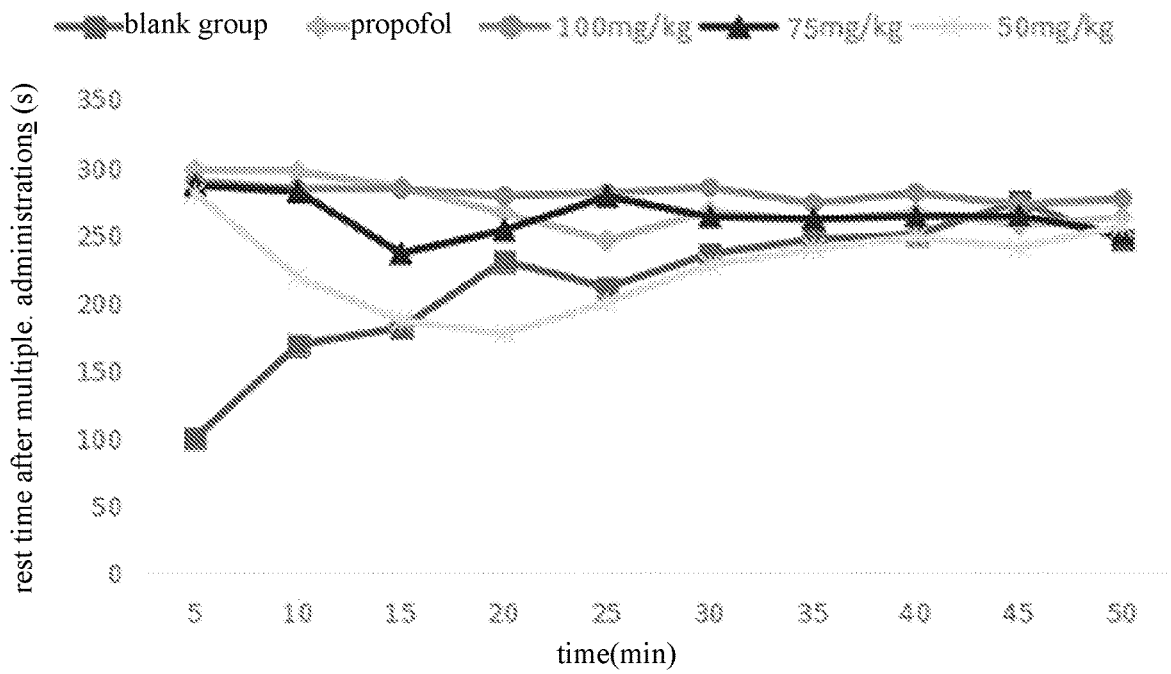
FIG. 5 shows the effect of multiple administrations of compound 1-2 in Example 27 on the rest time between mice's autonomous activities.
Figure 6:
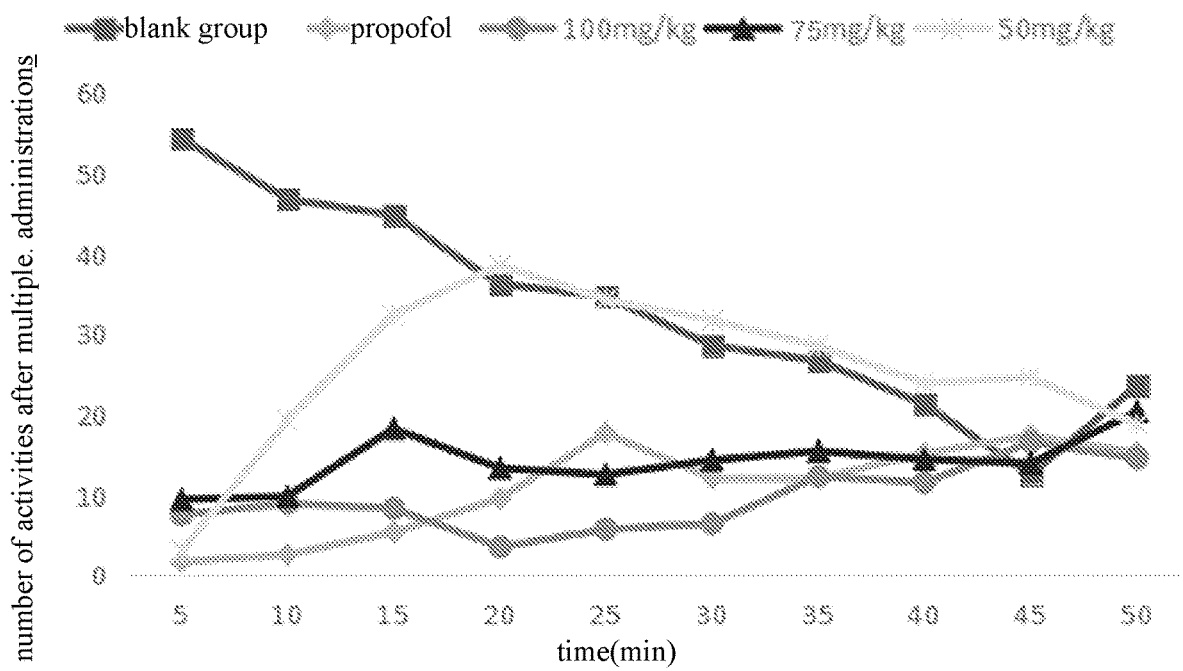
FIG. 6 shows the effect of multiple administrations of compound 1-2 in Example 27 on the number of mice's autonomous activities.

2. Effect of Multiple Administrations of Compound 1-2 on the Autonomous Activity of Mice During the test period, the autonomous activity of the mice in the blank group decreased slowly with the extension of the exploration time. After 10 consecutive injections of the drug, within 10 minutes, the autonomous activity of the mice in propofol group and compound 1-2 with each dose group had a significant reduction, which was manifested in the significant reduction in the total activity distance and the number of activities of the mice in each group and the significant increase in the rest time. In the positive drug propofol group, the autonomous activity basically recovered 40-45 minutes after administration (similar to the blank group at the same time). The autonomous activity of the mice in 50 mg/kg group of compound 1-2 returned to normal levels 15-20 min after administration (similar to the blank group at the same time); the autonomous activity of the mice in 75 mg/kg group of compound 1-2 returned to normal levels 40-45 min after administration (similar to the blank group at the same time); the autonomous activity of the mice in 100 mg/kg group of compound 1-2 did not return to normal levels during the test period (50 minutes) (similar to the blank group at the same time); see FIG. 4-6 for details.

It can be seen from FIG. 1-6 that: according to the total distance, the number of activities and the rest time of autonomous activity, it can be seen that the autonomous activity recovery with single-administration of propofol is slightly faster than that of the test drug, which is closer to the low-dose group of compound 1-2. However, the recovery of autonomous activity after multiple administrations of propofol was significantly slowed, which was basically the same as the recovery speed and degree of the tested drug with a dose of 75 mg/kg, but the test drug 75 mg/kg group was even better than propofol 20 mg/kg in the index of the number of activities and the rest time.

All literatures mentioned in the present invention are incorporated by reference herein, as though individually incorporated by reference. Additionally, it should be understood that after reading the above teaching, many variations and modifications may be made by the skilled in the art, and these equivalents also fall within the scope as defined by the appended claims.

The invention claimed is:

1. A compound of the following formula 1:

[Structure of Formula 1: benzodiazepine-imidazole core with substituents R, R₁, R₂ on benzene ring, OR₃ ester group, H₃C on imidazole, ·HX salt]

wherein:
R is F, Cl, Br, NO₂, C₁-C₆ alkyl, CF₃, or OCH₃;
R₁ is F, Cl, Br, NO₂, C₁-C₆ alkyl, CF₃, or OCH₃;
R₂ is

[Three pyridyl structures: 2-pyridyl, 3-pyridyl, or 4-pyridyl];

R₃ is C₁-C₆ alkyl; and
HX is a pharmaceutically acceptable inorganic acid or a pharmaceutically acceptable organic acid selected from the group consisting of hydrofluoric acid, hydrochloric acid, hydrobromic acid, nitric acid, phosphoric acid, sulfuric acid, formic acid, acetic acid, trifluoroacetic acid, propionic acid, oxalic acid, malonic acid, succinic acid, fumaric acid, maleic acid, lactic acid, malic acid, tartaric acid, citric acid, picric acid, benzoic acid, methanesulfonic acid, ethanesulfonic acid, benzenesulfonic acid, p-toluenesulfonic acid, and naphthalenesulfonic acid.

2. The compound according to claim 1, wherein R and R₁ are different.

3. The compound according to claim 1, wherein:
(i) R is C₁-C₆ alkyl; or
(ii) R₁ is C₁-C₆ alkyl.

4. The compound according to claim 1, wherein:
R is F;
R₁ is C₁-C₆ alkyl; and
R₂ is

[2-pyridyl structure].

5. The compound according to claim 1, wherein:
R is C₁-C₆ alkyl;
R₁ is F; and
R₂ is

[3-pyridyl structure].

6. The compound according to claim 1, wherein:
R is F;
R₁ is CH₃;
R₂ is

[2-pyridyl structure];

and
R₃ is CH₃, CH₂CH₃, CH₂CH₂CH₃, CH(CH₃)₂, CH₂CH₂CH₂CH₃, CH₂CH(CH₃)₂, C(CH₃)₃, CH₂CH₂CH₂CH₂CH₃, CH₂CH₂C(CH₃)₂, CH₂C(CH₃)₂CH₃, or CH₂CH₂CH₂CH₂CH₂CH₃.

7. The compound according to claim 1, wherein the compound is selected from the group consisting of:

Compound Number 1-1

[Structure of Compound 1-1 with benzenesulfonic acid salt]

Compound Number 1-2

[Structure of Compound 1-2 with p-toluenesulfonic acid salt]

Compound Number 1-3
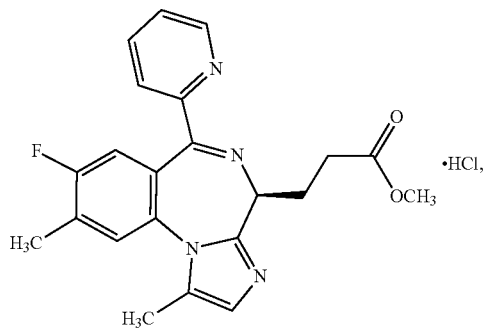
·HCl,
Compound Number 1-4
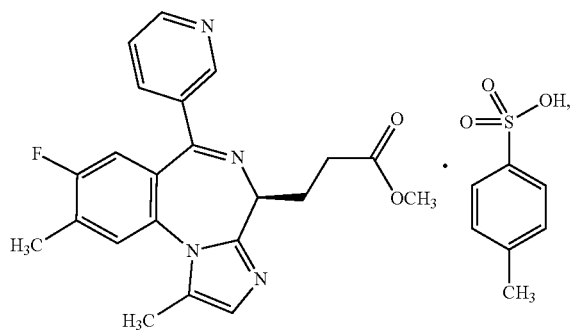
Compound Number 1-5
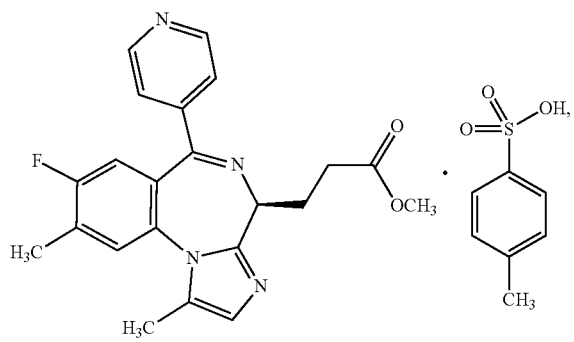
Compound Number 1-6
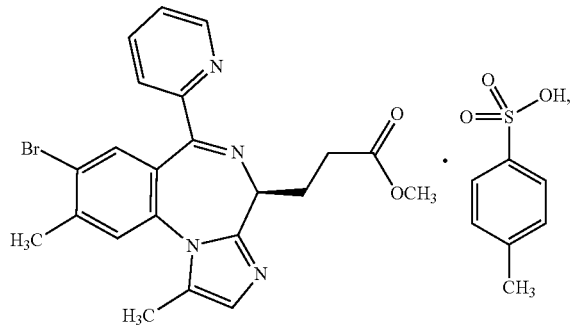
Compound Number 1-7
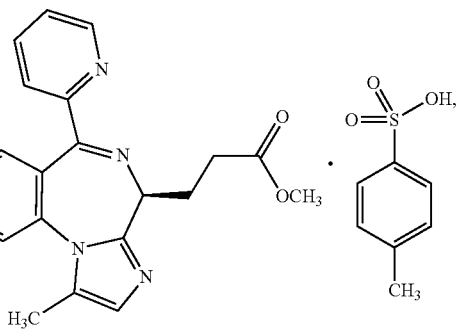
Compound Number 1-8
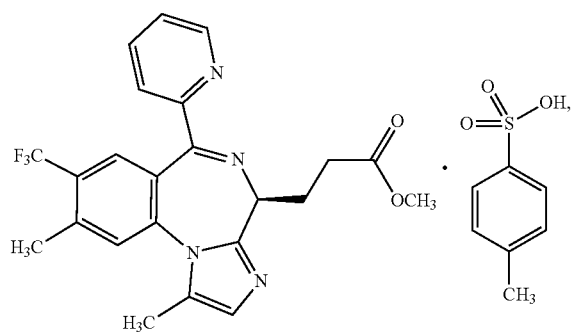
Compound Number 1-9
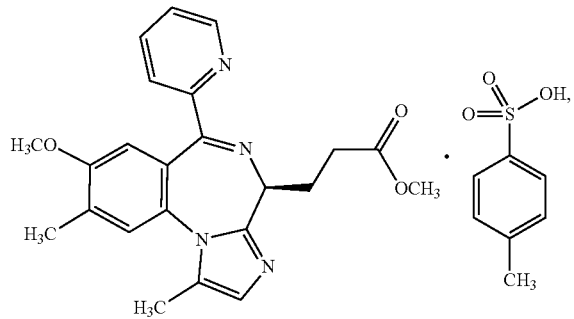
Compound Number 1-10
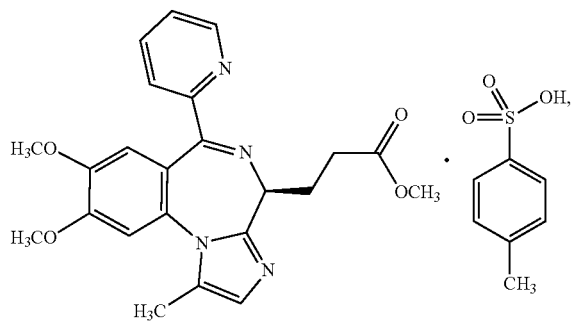

Compound Number 1-11
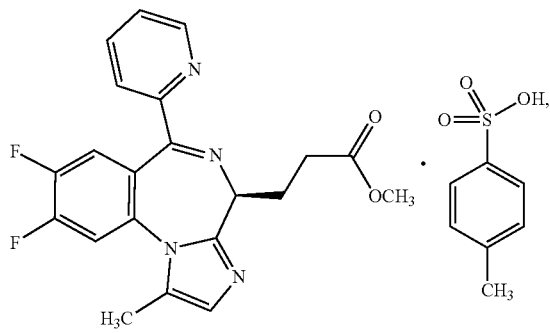

Compound Number 1-12
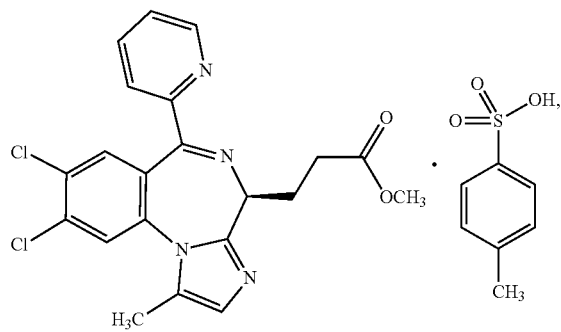

Compound Number 1-13
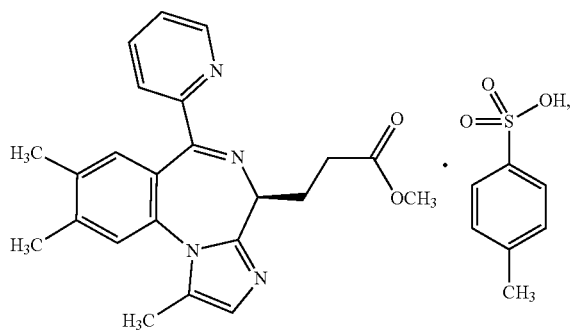

Compound Number 1-14
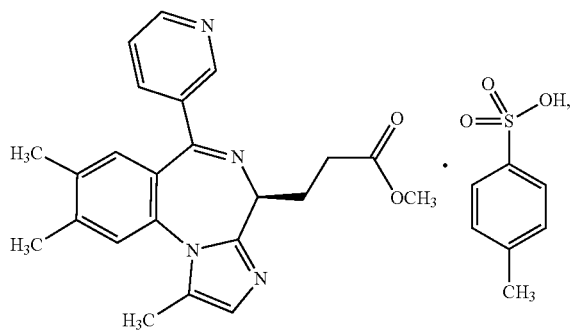

Compound Number 1-15
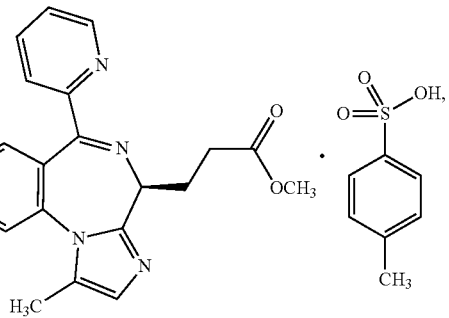

Compound Number 16
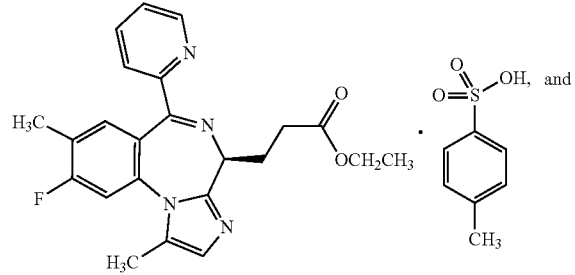

Compound Number 17
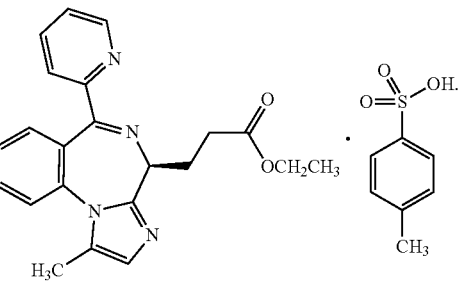

8. A pharmaceutical composition comprising a pharmaceutically acceptable carrier and an anesthetically effective amount of at least one compound according to claim 1.

9. A method for anesthetizing a subject in need thereof, wherein the method comprises administering to the subject an anesthetically effective amount of at least one compound according to claim 1.

10. A process for preparing a compound of the following formula 1 according to claim 1:

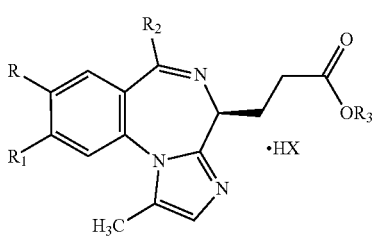

wherein:

R is F, Cl, Br, NO$_2$, C$_1$-C$_6$ alkyl, CF$_3$, or OCH$_3$;
R$_1$ is F, Cl, Br, NO$_2$, C$_1$-C$_6$ alkyl, CF$_3$, or OCH$_3$;
R$_2$ is

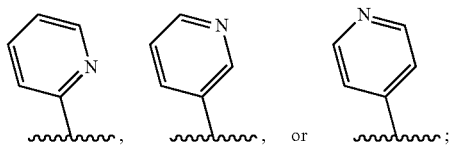 [SMILES: *c1ccccn1 ; *c1cccnc1 ; *c1ccncc1]

R$_3$ is C$_1$-C$_6$ alkyl; and
HX is a pharmaceutically acceptable inorganic acid or a pharmaceutically acceptable organic acid selected from the group consisting of hydrofluoric acid, hydrochloric acid, hydrobromic acid, nitric acid, phosphoric acid, sulfuric acid, formic acid, acetic acid, trifluoroacetic acid, propionic acid, oxalic acid, malonic acid, succinic acid, fumaric acid, maleic acid, lactic acid, malic acid, tartaric acid, citric acid, picric acid, benzoic acid, methanesulfonic acid, ethanesulfonic acid, benzenesulfonic acid, p-toluenesulfonic acid, and naphthalenesulfonic acid;

wherein the process comprises the following steps:

(1) reacting a compound of the following formula 2:

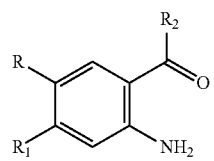

2 wherein:

R is F, Cl, Br, NO$_2$, C$_1$-C$_6$ alkyl, CF$_3$, or OCH$_3$;
R$_1$ is F, Cl, Br, NO$_2$, C$_1$-C$_6$ alkyl, CF$_3$, or OCH$_3$; and
R$_2$ is

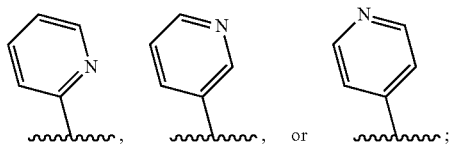 [SMILES: *c1ccccn1 ; *c1cccnc1 ; *c1ccncc1]

with a compound of the following formula 3:

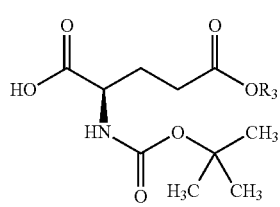

3 wherein:

R$_3$ is C$_1$-C$_6$ alkyl;

in the presence of dicyclohexyl carbodiimide (DCC), to provide a compound of the following formula 4:

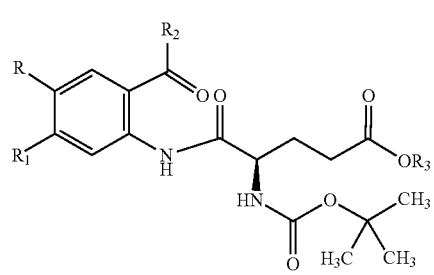

4 wherein:

R is F, Cl, Br, NO$_2$, C$_1$-C$_6$ alkyl, CF$_3$, or OCH$_3$;
R$_1$ is F, Cl, Br, NO$_2$, C$_1$-C$_6$ alkyl, CF$_3$, or OCH$_3$;
R$_2$ is

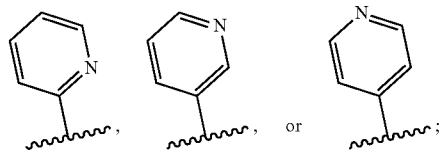 [SMILES: *c1ccccn1 ; *c1cccnc1 ; *c1ccncc1]

and

R$_3$ is C$_1$-C$_6$ alkyl;

(2) reacting the compound of the formula 4 above with an acid of the following formula 5:

HX                                   5 wherein:

HX is a pharmaceutically acceptable inorganic acid or a pharmaceutically acceptable organic acid selected from the group consisting of hydrofluoric acid, hydrochloric acid, hydrobromic acid, nitric acid, phosphoric acid, sulfuric acid, formic acid, acetic acid, trifluoroacetic acid, propionic acid, oxalic acid, malonic acid, succinic acid, fumaric acid, maleic acid, lactic acid, malic acid, tartaric acid, citric acid, picric acid, benzoic acid, methanesulfonic acid, ethanesulfonic acid, benzenesulfonic acid, p-toluenesulfonic acid, and naphthalenesulfonic acid;

to provide a compound of the following formula 6:

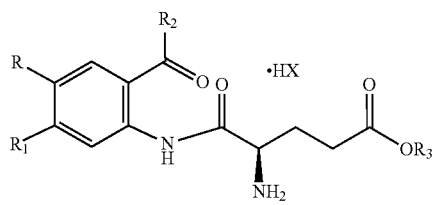

6 wherein:
R is F, Cl, Br, $NO_2$, $C_1$-$C_6$ alkyl, $CF_3$, or $OCH_3$;
$R_1$ is F, Cl, Br, $NO_2$, $C_1$-$C_6$ alkyl, $CF_3$, or $OCH_3$;
$R_2$ is

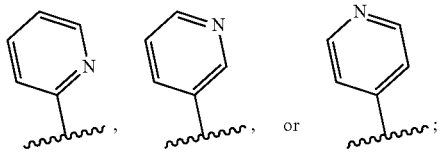 [SMILES: *c1ccccn1 ; *c1cccnc1 ; *c1ccncc1]

$R_3$ is $C_1$-$C_6$ alkyl; and

HX is a pharmaceutically acceptable inorganic acid or a pharmaceutically acceptable organic acid selected from the group consisting of hydrofluoric acid, hydrochloric acid, hydrobromic acid, nitric acid, phosphoric acid, sulfuric acid, formic acid, acetic acid, trifluoroacetic acid, propionic acid, oxalic acid, malonic acid, succinic acid, fumaric acid, maleic acid, lactic acid, malic acid, tartaric acid, citric acid, picric acid, benzoic acid, methanesulfonic acid, ethanesulfonic acid, benzenesulfonic acid, p-toluenesulfonic acid, and naphthalenesulfonic acid;

(3) reacting the compound of the formula 6 above with sodium bicarbonate ($NaHCO_3$), to provide a compound of the following formula 7:

7

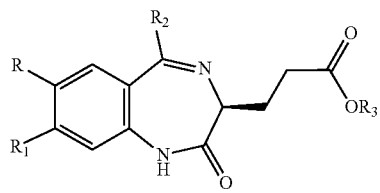

wherein:
R is F, Cl, Br, $NO_2$, $C_1$-$C_6$ alkyl, $CF_3$, or $OCH_3$;
$R_1$ is F, Cl, Br, $NO_2$, $C_1$-$C_6$ alkyl, $CF_3$, or $OCH_3$;
$R_2$ is

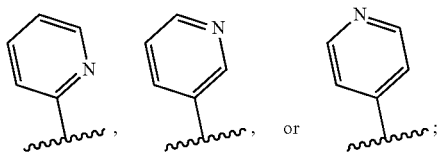 [SMILES: *c1ccccn1 ; *c1cccnc1 ; *c1ccncc1]

and
$R_3$ is $C_1$-$C_6$ alkyl;

(4) reacting the compound of the formula 7 above with a compound of the following formula 8:

8

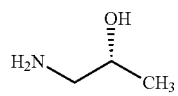

to provide a compound of the following formula 9:

9

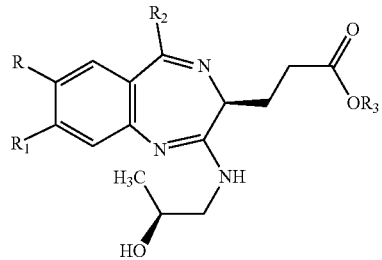

wherein:
R is F, Cl, Br, $NO_2$, $C_1$-$C_6$ alkyl, $CF_3$, or $OCH_3$;
$R_1$ is F, Cl, Br, $NO_2$, $C_1$-$C_6$ alkyl, $CF_3$, or $OCH_3$;
$R_2$ is

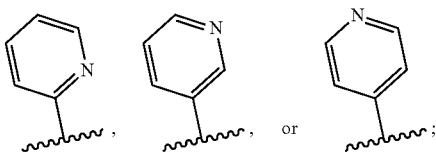 [SMILES: *c1ccccn1 ; *c1cccnc1 ; *c1ccncc1]

and
$R_3$ is $C_1$-$C_6$ alkyl;

(5) reacting the compound of the formula 9 above with Dess-Martin periodinane (DMP), to provide a compound of the following formula 10:

10

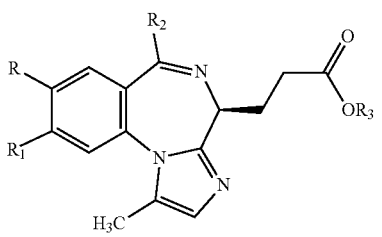

wherein:
R is F, Cl, Br, $NO_2$, $C_1$-$C_6$ alkyl, $CF_3$, or $OCH_3$;
$R_1$ is F, Cl, Br, $NO_2$, $C_1$-$C_6$ alkyl, $CF_3$, or $OCH_3$;
$R_2$ is

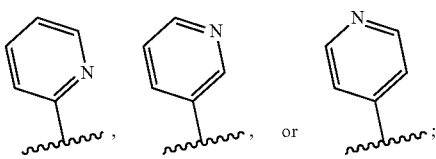 [SMILES: *c1ccccn1 ; *c1cccnc1 ; *c1ccncc1]

and
$R_3$ is $C_1$-$C_6$ alkyl; and (6) reacting the compound of the formula 10 above with an acid of the following formula 5:

HX  5 wherein:
HX is a pharmaceutically acceptable inorganic acid or a pharmaceutically acceptable organic acid selected from the group consisting of hydrofluoric acid, hydrochloric acid, hydrobromic acid, nitric acid, phosphoric acid, sulfuric acid, formic acid, acetic acid, trifluoroacetic acid, propionic acid, oxalic acid, malonic acid, succinic acid, fumaric acid, maleic acid, lactic acid, malic acid, tartaric acid, citric acid, picric acid, benzoic acid, methanesulfonic acid, ethanesulfonic acid, benzenesulfonic acid, p-toluenesulfonic acid, and naphthalenesulfonic acid;

to provide the compound of the following formula 1 above:

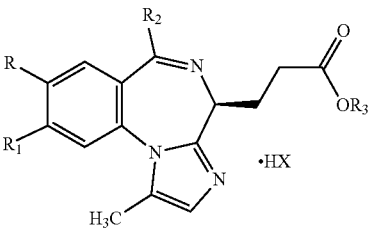

wherein:
R is F, Cl, Br, NO$_2$, C$_1$-C$_6$ alkyl, CF$_3$, or OCH$_3$;
R$_1$ is F, Cl, Br, NO$_2$, C$_1$-C$_6$ alkyl, CF$_3$, or OCH$_3$;
R$_2$ is

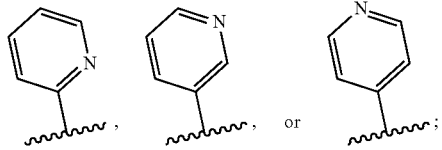 [SMILES: *c1ccccn1 ; *c1cccnc1 ; *c1ccncc1]

R$_3$ is C$_1$-C$_6$ alkyl; and
HX is a pharmaceutically acceptable inorganic acid or a pharmaceutically acceptable organic acid selected from the group consisting of hydrofluoric acid, hydrochloric acid, hydrobromic acid, nitric acid, phosphoric acid, sulfuric acid, formic acid, acetic acid, trifluoroacetic acid, propionic acid, oxalic acid, malonic acid, succinic acid, fumaric acid, maleic acid, lactic acid, malic acid, tartaric acid, citric acid, picric acid, benzoic acid, methanesulfonic acid, ethanesulfonic acid, benzenesulfonic acid, p-toluenesulfonic acid, and naphthalenesulfonic acid.

11. A compound of the following formula 10:

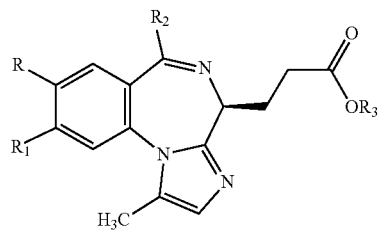

wherein:
R is F, Cl, Br, NO$_2$, C$_1$-C$_6$ alkyl, CF$_3$, or OCH$_3$;
R$_1$ is F, Cl, Br, NO$_2$, C$_1$-C$_6$ alkyl, CF$_3$, or OCH$_3$;
R$_2$ is

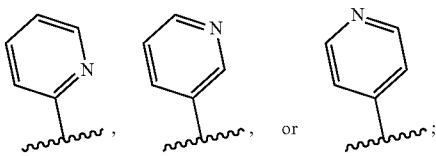 [SMILES: *c1ccccn1 ; *c1cccnc1 ; *c1ccncc1]

and
R$_3$ is C$_1$-C$_6$ alkyl.

12. A pharmaceutical composition comprising a pharmaceutically acceptable carrier and an anesthetically effective amount of at least one compound according to claim 11.

* * * * *